(12) United States Patent
Sixto, Jr. et al.

(10) Patent No.: US 8,568,462 B2
(45) Date of Patent: Oct. 29, 2013

(54) BONE PLATE SYSTEM WITH TWO DIFFERENT TYPES OF DRILL GUIDES

(75) Inventors: Robert Sixto, Jr., Miami, FL (US); Juergen A. Kortenbach, Miami Springs, FL (US); Jose Luis Francese, Miami Springs, FL (US)

(73) Assignee: Biomet C.V., Gibraltar (GI)

( * ) Notice: Subject to any disclaimer, the term of this patent is extended or adjusted under 35 U.S.C. 154(b) by 395 days.

(21) Appl. No.: 12/261,392

(22) Filed: Oct. 30, 2008

(65) Prior Publication Data

US 2009/0118768 A1 May 7, 2009

Related U.S. Application Data

(60) Provisional application No. 60/985,000, filed on Nov. 2, 2007.

(51) Int. Cl.
*A61B 17/80* (2006.01)
(52) U.S. Cl.
USPC ........... 606/280; 606/281; 606/284; 606/285; 606/96; 606/86 R
(58) Field of Classification Search
USPC .................... 606/280, 297, 291, 284, 286, 96
See application file for complete search history.

(56) References Cited

U.S. PATENT DOCUMENTS

| | | |
|---|---|---|
| 1,105,105 A | 7/1914 | Sherman |
| 3,593,709 A | 7/1971 | Halloran |
| 4,219,015 A | 8/1980 | Steinemann |
| 4,905,680 A * | 3/1990 | Tunc .............................. 606/280 |
| 4,966,599 A | 10/1990 | Pollock |
| 5,002,544 A | 3/1991 | Klaue et al. |
| 5,053,036 A | 10/1991 | Perren |
| 5,336,224 A | 8/1994 | Selman |
| 5,360,448 A | 11/1994 | Thramann |
| 5,372,598 A | 12/1994 | Luhr |
| 5,718,705 A | 2/1998 | Sammarco |
| 5,752,958 A | 5/1998 | Wellisz |
| 5,785,712 A | 7/1998 | Runciman et al. |
| 5,807,396 A | 9/1998 | Raveh |
| 5,935,128 A | 8/1999 | Carter et al. |
| 5,954,722 A * | 9/1999 | Bono ............................ 606/281 |
| 5,984,925 A | 11/1999 | Apgar |
| 6,001,099 A | 12/1999 | Huebner |

(Continued)

FOREIGN PATENT DOCUMENTS

| | | |
|---|---|---|
| DE | 4343117 | 6/1995 |
| DE | 20200705 U1 | 3/2002 |

(Continued)

*Primary Examiner* — Sameh Boles
*Assistant Examiner* — Samuel Hanna
(74) *Attorney, Agent, or Firm* — Gordon & Jacobson, PC

(57) ABSTRACT

A system for the internal fixation of a fractured bone of an elbow joint of a patient includes at least one bone plate, each bone plate having a plurality of holes and generally configured to fit an anatomical surface of the fractured bone. The at least one plate is adapted to be customized to the shape of a patient's bone. The system also includes a plurality of fasteners including at least one locking fastener for attaching the bone plate to the bone. At least one of the holes is a threaded hole. Guides for plate benders, drills, and/or K-wires can be pre-assembled to the threaded holes, and the locking fastener can lock into any of the threaded holes after the guides are removed.

14 Claims, 24 Drawing Sheets

(56) References Cited

U.S. PATENT DOCUMENTS

| | | | |
|---|---|---|---|
| 6,123,709 A | 9/2000 | Jones | |
| 6,129,730 A * | 10/2000 | Bono et al. | 606/291 |
| 6,162,243 A | 12/2000 | Gray et al. | |
| 6,162,253 A | 12/2000 | Conzemius et al. | |
| 6,306,171 B1 | 10/2001 | Conzemius | |
| 6,348,052 B1 | 2/2002 | Sammarco | |
| 6,364,881 B1 | 4/2002 | Apgar | |
| 6,379,364 B1 * | 4/2002 | Brace et al. | 606/96 |
| 6,652,530 B2 | 11/2003 | Ip | |
| 6,663,632 B1 | 12/2003 | Frigg | |
| 6,730,091 B1 | 5/2004 | Pfefferle et al. | |
| 6,866,665 B2 | 3/2005 | Orbay | |
| 6,960,211 B1 | 11/2005 | Pfefferle et al. | |
| 6,960,216 B2 * | 11/2005 | Kolb et al. | 606/96 |
| 6,972,020 B1 | 12/2005 | Grayson et al. | |
| 7,090,676 B2 | 8/2006 | Huebner et al. | |
| 7,128,744 B2 | 10/2006 | Weaver | |
| 7,179,260 B2 | 2/2007 | Gerlach | |
| 7,189,237 B2 | 3/2007 | Huebner | |
| 7,488,326 B2 * | 2/2009 | Elliott | 606/96 |
| 7,625,378 B2 * | 12/2009 | Foley | 606/96 |
| 7,727,264 B2 * | 6/2010 | Orbay et al. | 606/280 |
| 7,736,380 B2 * | 6/2010 | Johnston et al. | 606/280 |
| 7,776,047 B2 * | 8/2010 | Fanger et al. | 606/96 |
| 7,780,664 B2 * | 8/2010 | Orbay | 606/62 |
| 7,909,829 B2 * | 3/2011 | Patel et al. | 606/86 A |
| 7,909,848 B2 * | 3/2011 | Patel et al. | 606/201 |
| 7,914,531 B1 | 3/2011 | Geller et al. | |
| 7,935,123 B2 * | 5/2011 | Fanger et al. | 606/96 |
| 8,172,854 B2 * | 5/2012 | Blain et al. | 606/96 |
| 2002/0128654 A1 | 9/2002 | Steger et al. | |
| 2002/0156474 A1 | 10/2002 | Wack | |
| 2003/0055429 A1 | 3/2003 | Ip et al. | |
| 2003/0083667 A1 * | 5/2003 | Ralph et al. | 606/96 |
| 2004/0097937 A1 | 5/2004 | Pike et al. | |
| 2004/0102777 A1 | 5/2004 | Huebner | |
| 2004/0116930 A1 | 6/2004 | O'Driscoll | |
| 2004/0186482 A1 * | 9/2004 | Kolb et al. | 606/96 |
| 2004/0193155 A1 | 9/2004 | Castaneda | |
| 2004/0210220 A1 | 10/2004 | Tornier | |
| 2005/0010226 A1 | 1/2005 | Grady et al. | |
| 2005/0011659 A1 | 1/2005 | Tempelman et al. | |
| 2005/0049710 A1 | 3/2005 | O'Driscoll et al. | |
| 2005/0059971 A1 | 3/2005 | Michelson | |
| 2005/0085824 A1 * | 4/2005 | Castaneda | 606/98 |
| 2005/0086939 A1 | 4/2005 | Schmid | |
| 2005/0090825 A1 | 4/2005 | Pfefferle | |
| 2005/0216090 A1 | 9/2005 | O'Driscoll et al. | |
| 2005/0228398 A1 * | 10/2005 | Rathbun et al. | 606/96 |
| 2005/0234467 A1 * | 10/2005 | Rains | 606/96 |
| 2005/0261688 A1 | 11/2005 | Grady | |
| 2006/0036249 A1 | 2/2006 | Baynham et al. | |
| 2006/0100625 A1 * | 5/2006 | Ralph et al. | 606/69 |
| 2006/0116679 A1 * | 6/2006 | Lutz et al. | 606/69 |
| 2006/0149250 A1 | 7/2006 | Castaneda et al. | |
| 2006/0161158 A1 * | 7/2006 | Orbay et al. | 606/69 |
| 2006/0173458 A1 | 8/2006 | Forstein et al. | |
| 2006/0173459 A1 | 8/2006 | Kay et al. | |
| 2006/0195104 A1 | 8/2006 | Schlafli | |
| 2006/0200145 A1 | 9/2006 | Kay et al. | |
| 2006/0217722 A1 | 9/2006 | Dutoit | |
| 2006/0229618 A1 | 10/2006 | Dube | |
| 2006/0264949 A1 | 11/2006 | Kohut et al. | |
| 2007/0225714 A1 | 9/2007 | Gradl | |
| 2007/0233111 A1 | 10/2007 | Orbay et al. | |
| 2007/0233112 A1 * | 10/2007 | Orbay et al. | 606/69 |
| 2008/0009951 A1 | 1/2008 | Hodge | |

FOREIGN PATENT DOCUMENTS

| | | |
|---|---|---|
| EP | 471419 A2 | 2/1992 |
| EP | 1211992 | 6/2002 |
| EP | 1423057 | 6/2004 |
| EP | 1654994 A1 | 10/2006 |
| FR | 2233973 A1 | 1/1975 |
| FR | 2405062 A1 | 5/1979 |
| WO | WO2004024009 | 3/2004 |
| WO | WO2005020851 | 3/2005 |
| WO | WO2005023127 | 3/2005 |

* cited by examiner

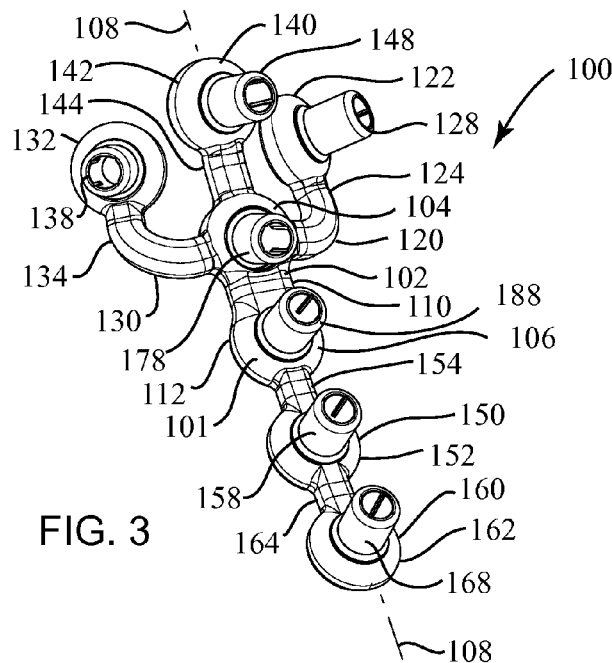
FIG. 3
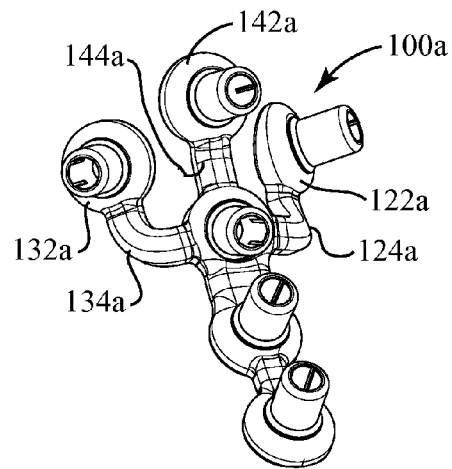
FIG. 3A
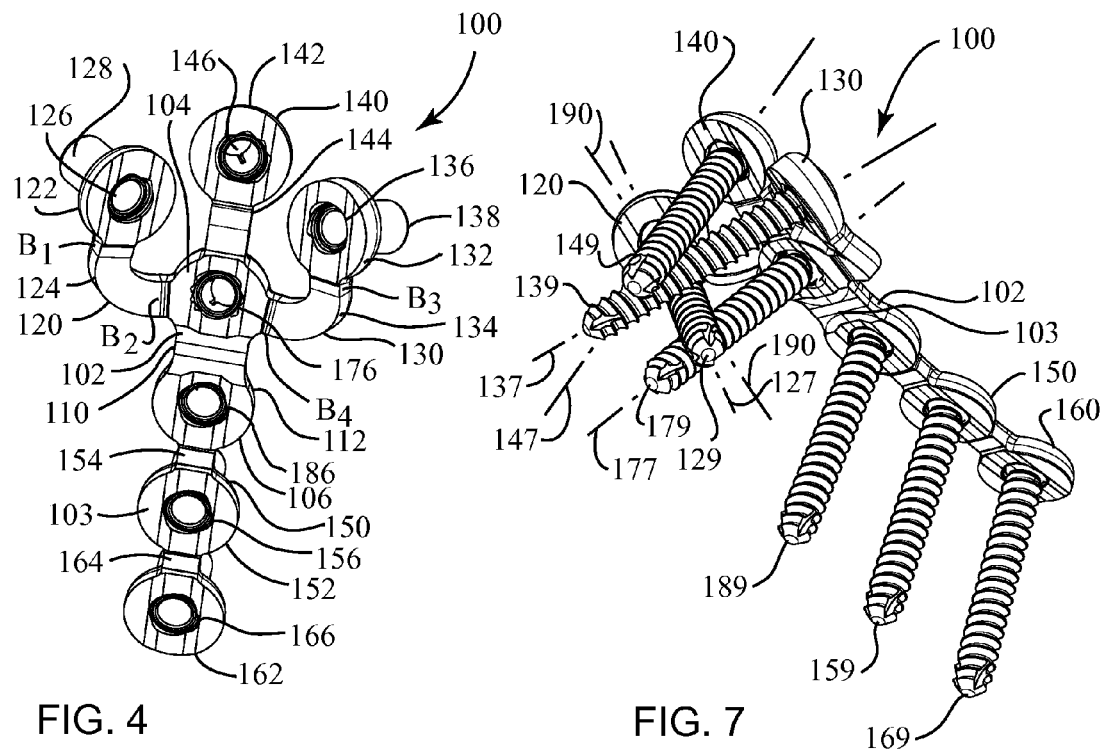
FIG. 4
FIG. 7

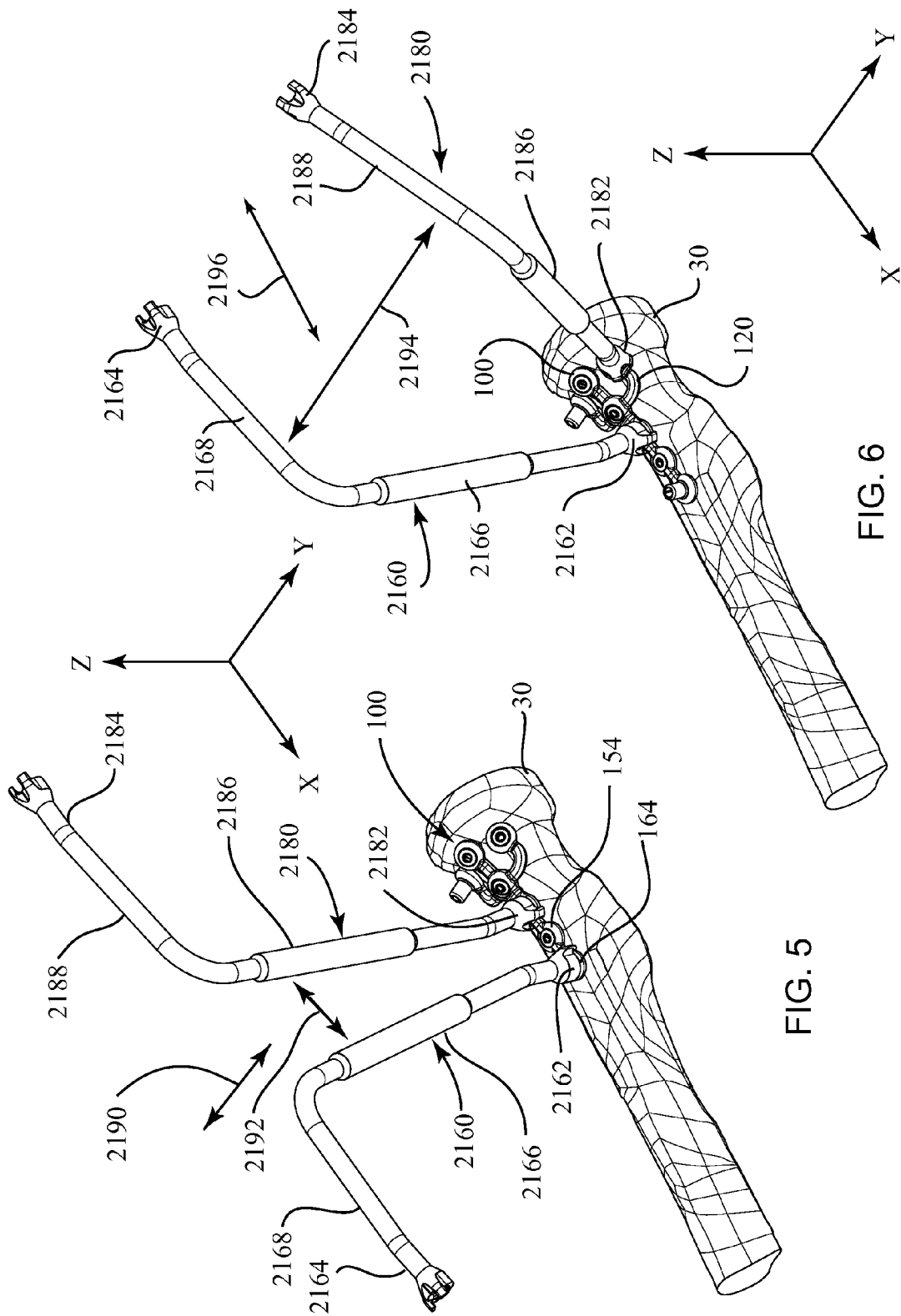

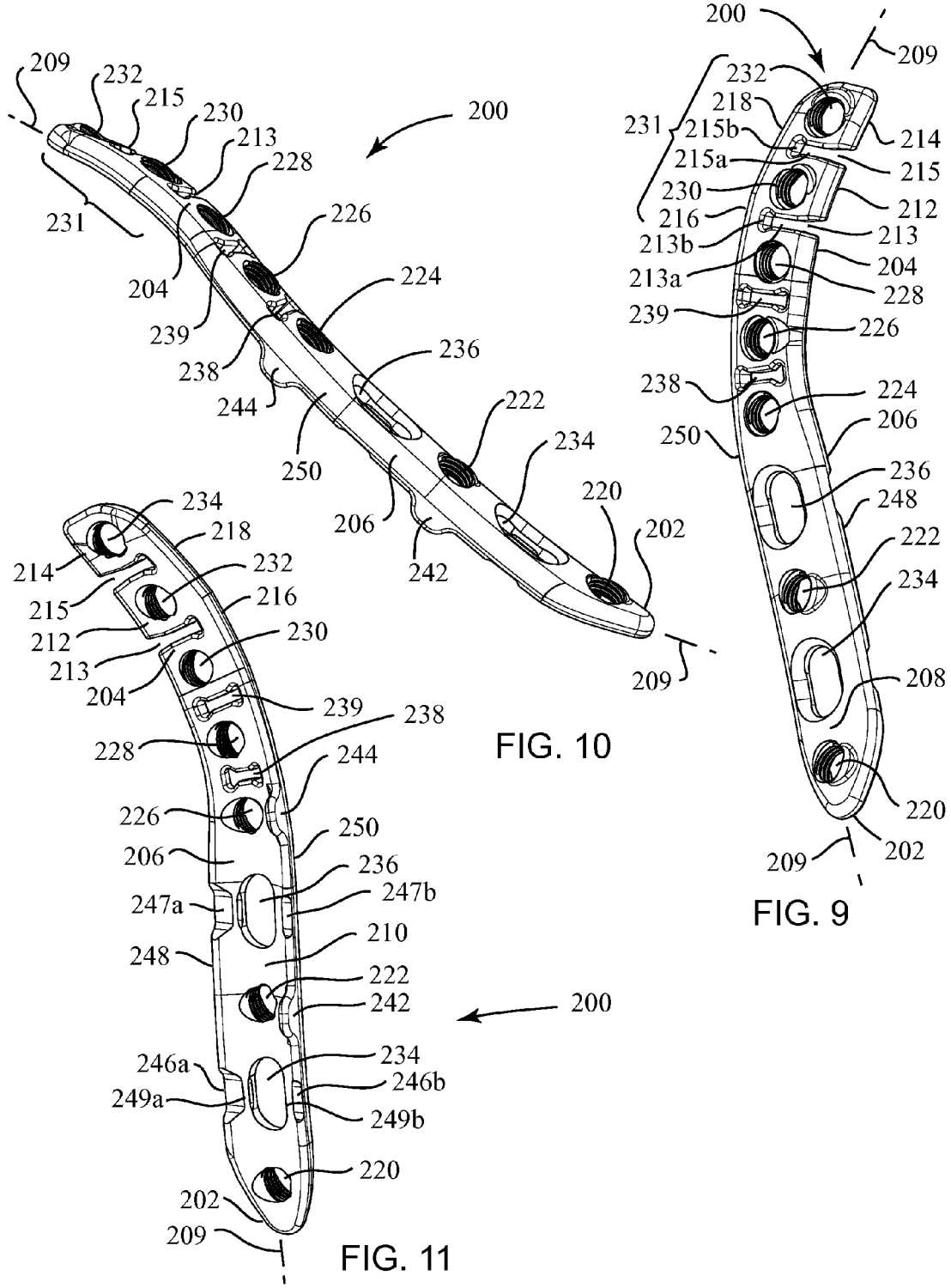

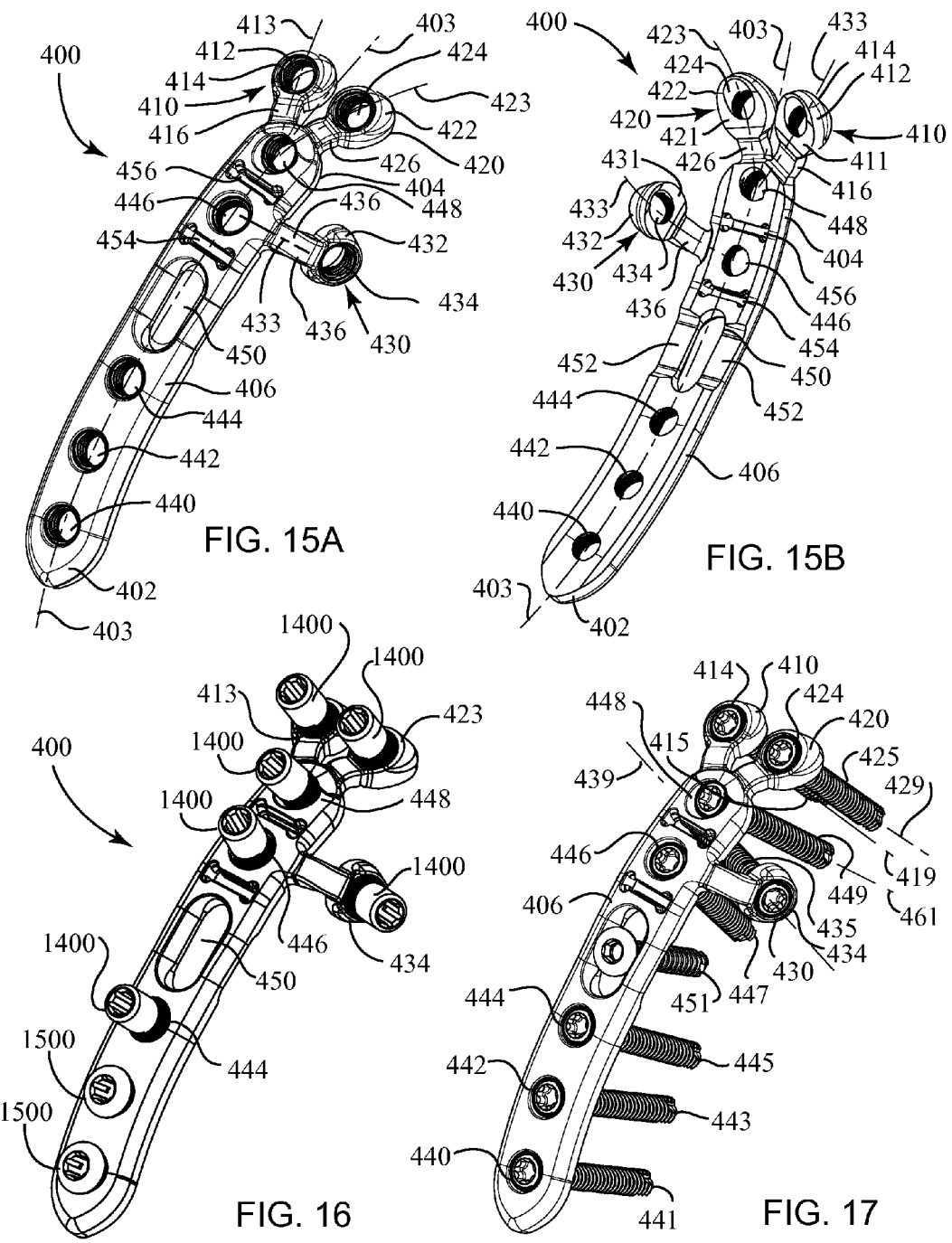

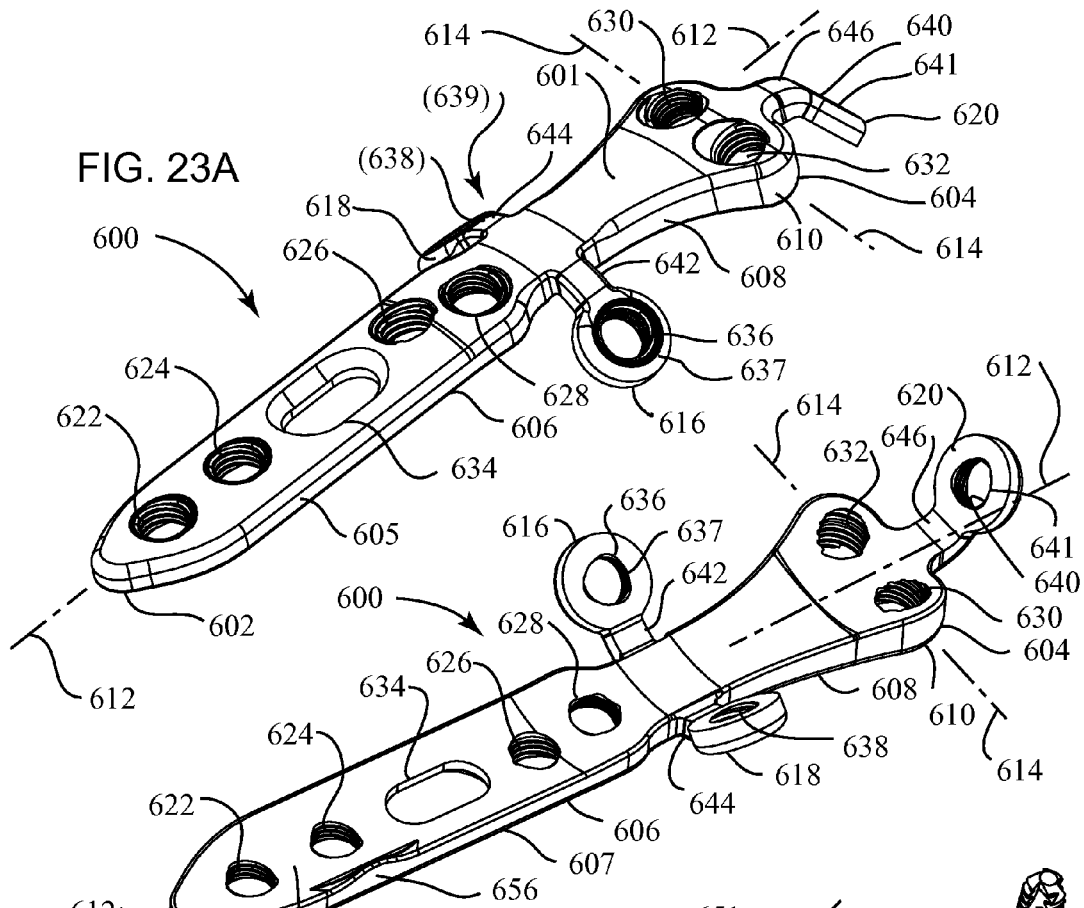
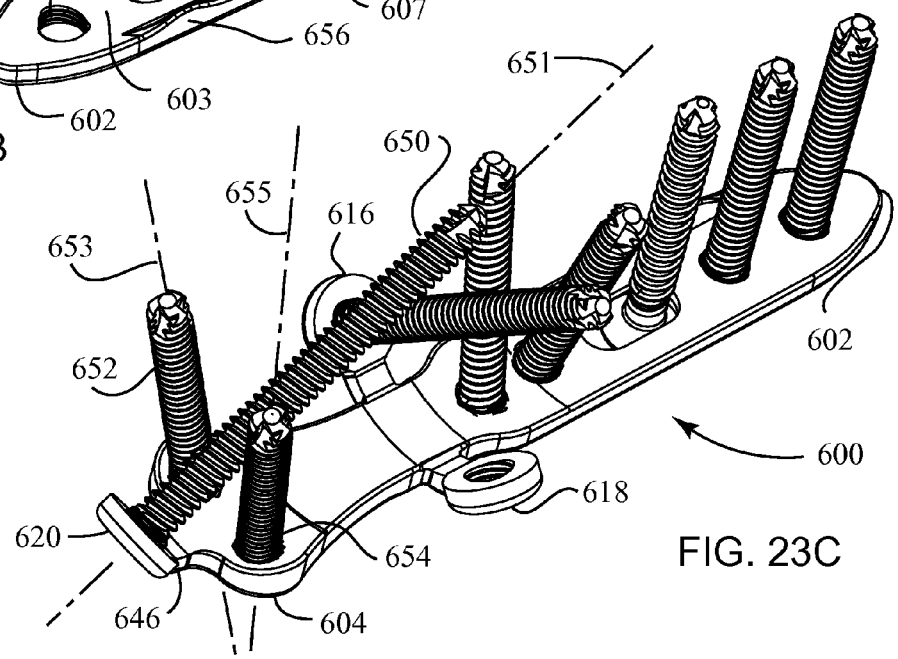
FIG. 23A
FIG. 23B
FIG. 23C

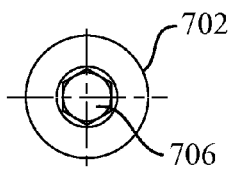
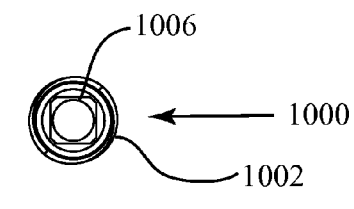
FIG. 27  FIG. 29
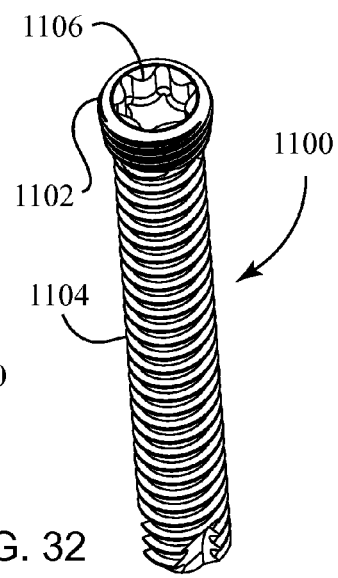
FIG. 32
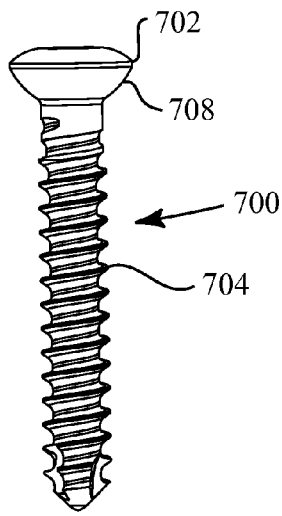
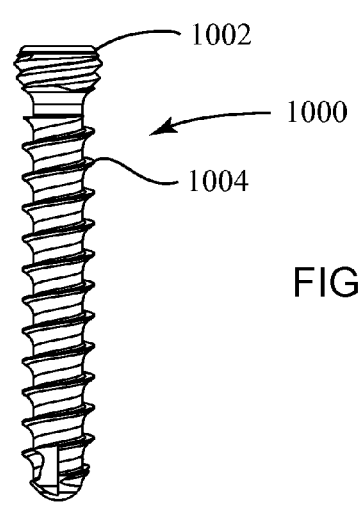
FIG. 28  FIG. 30
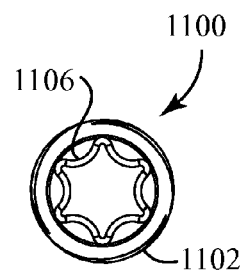
FIG. 33
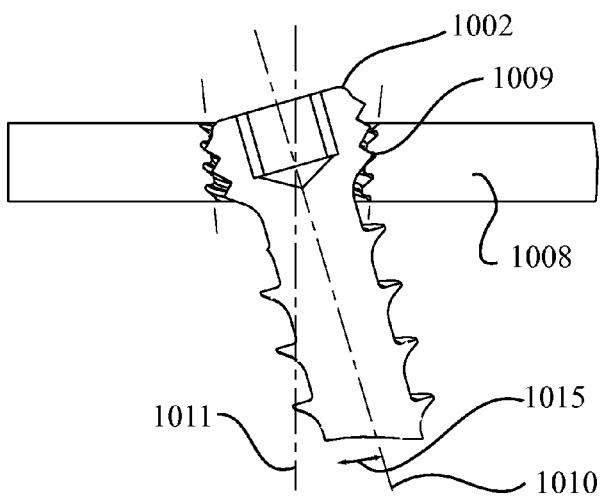
FIG. 31
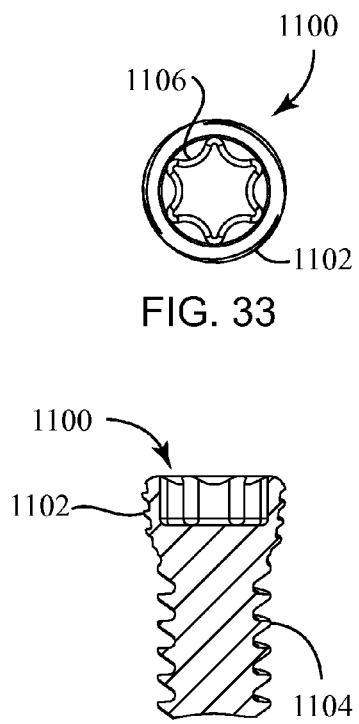
FIG. 34

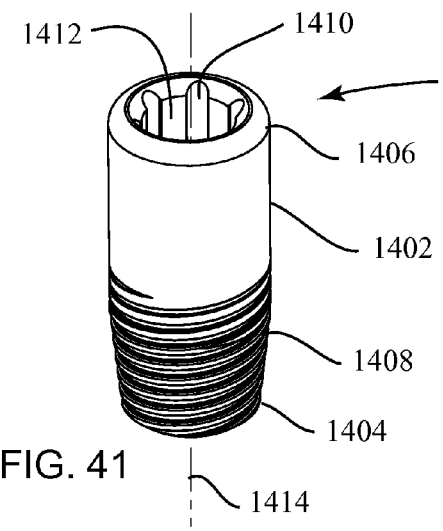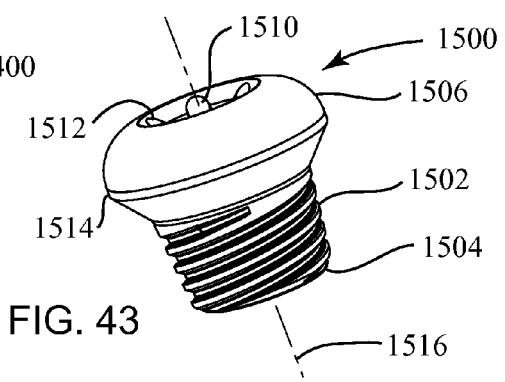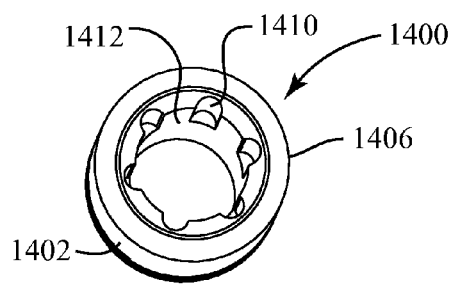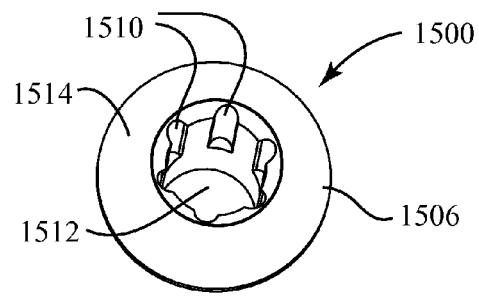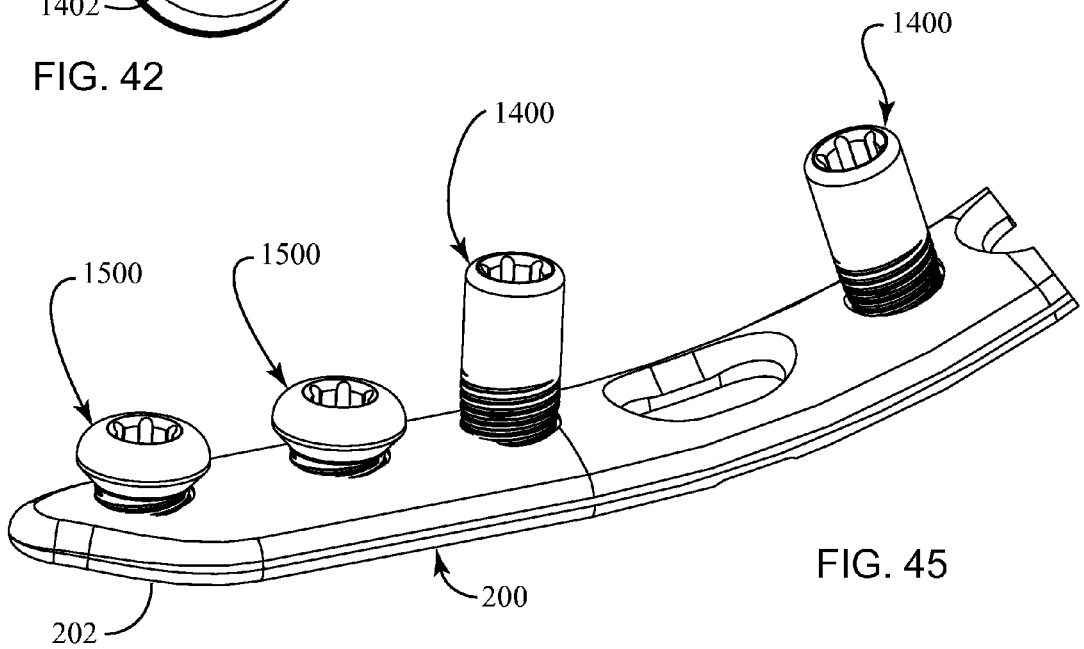
FIG. 41
FIG. 42
FIG. 43
FIG. 44
FIG. 45 ate the bone plate inside the patient's body during the surgical procedure.

BONE PLATE SYSTEM WITH TWO DIFFERENT TYPES OF DRILL GUIDES

CROSS-REFERENCE TO RELATED APPLICATION

This application claims benefit of Ser. No. 60/985,000, filed Nov. 2, 2007, which is hereby incorporated by reference herein in its entirety.

FIELD OF THE INVENTION

The subject matter of this disclosure relates broadly to surgical devices and methods for the internal fixation of fractured bones, and more particularly, to bone plates and fasteners.

BACKGROUND OF THE INVENTION

The three long bones of the upper extremity are the humerus, radius and ulna. The distal portion of the humerus and the proximal portions of the radius and the ulna form the elbow joint. Elbow fractures account for only about 5-8% of all fractures and occur most commonly in older people as a result of a fall. The functional outcomes of elbow fractures often include high rates of joint stiffness, loss of range of motion and non-union.

Orthopedic surgeons generally follow certain principles for the proper internal fixation of the bones of the elbow joint. Each screw used to attach the plate to the bone should be as long as possible and engage as many articular fragments as possible. The screws should lock to the plate and interdigitate to create a "fixed angle" structure. The plate must be strong and stiff enough to not break or bend under load. Adhering to these principles for elbow fracture repair is particularly challenging given the difficulty of the surgical procedure and the anatomical variation among patients.

In addition, a bone plate attached to the surface of a fractured bone of the elbow joint may tend to stand "proud" of the bone surface. Currently available plates do not fit well on the bone surfaces without impinging on soft tissue or obstructing the natural articulation of the joint. One bone plate shape, even if provided for each type of elbow fracture and in different sizes, cannot accommodate all the anatomical differences among patients.

About half of all elbow fractures are radial head fractures and about a fifth involve fracture of the radial neck or proximal radius. Because of the considerations just stated, surgeons generally prefer not to use bone plates to treat the fractured proximal radius. Depending on the extent of comminution of proximal radius fractures, surgeons may instead use external fixation or screws and pins together with post operative therapy.

Fractures of the coronoid, which is located on the proximal ulna, are typically small but difficult to treat. Proper treatment is important since the coronoid fracture may have a heavy impact on overall elbow stability. Traditional fixation of these fractures involve capture of the coronoid fragments with screws or sutures coming from the posterior side of the ulna. This type of fixation may not be stable enough to resist the strong anterior dislocating force of the distal humerus.

The olecranon is located on the posterior side of the proximal end of the ulna and articulates in the olecranon fossa. The olecranon is not covered with thick layers of soft tissue and is particularly vulnerable to external impacts and fracture. The olecranon also is the attachment location of the triceps muscle used in extension of the arm, and transfers very high forces.

In addition to fractures of the olecranon, the surgeon may intentionally sever the olecranon from the proximal ulna during an osteotomy procedure in order to reflect the triceps muscle, thereby obtaining improved surgical access to the distal humerus. Once the repair to the humerus has been completed, the surgeon then may use a bone plate to reattach the olecranon to the proximal ulna.

Currently available fracture fixation plates for the medial, lateral and posterolateral parts of the distal humerus do not consistently match the contour of the bone surface. Due to the anatomical differences between patients, a single bone plate configuration, as initially provided to the surgeon, is unlikely to conform perfectly to the bone surface, even if that plate was specifically designed for that particular type of bone. Therefore, some manufacturers provide numerous sizes and configurations of bone plates for a particular portion of a specific bone. Since selecting the right plate involves subjectivity, clinical outcomes may not be highly consistent.

SUMMARY OF THE INVENTION

A system of bendable plates is provided that may be easily and safely reconfigured inside the patient's body (in situ) during the surgical procedure. The system can be reconfigured without distorting the shape of bone fastener holes in the plate, and any threads within the holes. The system includes and is adapted for use with in situ bending tools to reconfigure the plate inside the patient's body during the surgical procedure.

A system of low profile bone plates and fasteners are provided for the internal fixation of the fractured bones of the elbow. The elbow joint is not protected with thick layers of soft tissue. The plates of the system of the invention have minimal thickness and conform closely to the bone surface. In addition, it is very important that the heads of all fasteners used to attach the plate to the bone not protrude significantly, if at all, above the top surface of the plate. A "proud" fastener head may lead to soft tissue irritation, inflammation or other types of trauma that may cause complications and patient discomfort.

An elbow fracture fixation system is provided that also includes locking fasteners for attachment of the bone plate to the fractured bone. In general, the primary functions of various bone plates of the system (which are all adjacent near the elbow joint) include not only holding the bone fragments together in healing alignment, but also the transfer of forces from the metaphysis to the diaphysis of the fractured bone while the bone is mending. The system allows the distal tip of a fastener to be anchored into healthy, cortical bone, and the transfer of force from the healthy bone to the plate, such that the plate properly accomplishes load sharing.

A system for elbow fixation is provided with includes a number of locking fasteners, each having an optimal trajectory, directly beneath the articulation surface of the fractured bone to create a scaffold for transferring forces from the articulating surface to the bone plate.

A system for the internal fixation of a fractured bone of an elbow joint of a patient has at least one bone plate, each bone plate having a plurality of holes and configured to fit an anatomical surface of the fractured bone. The system also has a plurality of fasteners including at least one locking fastener for attaching the bone plate to the bone. At least one of the holes is a threaded hole and the locking fastener can lock into the threaded hole.

The locking fastener may be a fixed-angle locking fastener or a multidirectional locking fastener. The system may also have at least one non-locking fastener and the threaded hole can receive the non-locking fastener. The non-locking fastener may be a multidirectional compression fastener. The bone plate may also have a plurality of threaded holes and a plurality of drill guides. Each drill guide has a bore sized for guiding a drill and a proximal portion that is engageable with a tool for removal of the drill guide from the threaded hole. Each drill guide is removably preassembled into one of the plurality of threaded holes. The system also may have a first bending tool and a second bending tool. Each bending tool has an elongated rod having a handle and an end effector at one end of the elongated rod and adapted for removable engagement to the drill guide. A user may removably attach the first bending tool to one of the drill guides and the second bending tool to another of the drill guides and then simultaneously apply a leveraging force to each of the first and second bending tools, thereby reconfiguring the bone plate. The bone plate of the system may be at least one of a radial plate for fixation of the proximal radius bone, an olecranon plate for fixation of the olecranon of the proximal ulna bone, a coronoid plate for fixation of the coronoid process of the proximal ulna bone, a lateral plate for fixation of the lateral distal humerus bone, a medial plate for fixation of the medial distal humerus bone, and a posterolateral plate for fixation of the posterolateral distal humerus bone.

According to another aspect of the system, a bone plate for the proximal radius has a rigid body with proximal and distal ends defining a longitudinal axis, a medial edge and a lateral edge. The bone plate also has a first arm extending from the rigid body. The first arm has a first ring element attached to the body by a first curved bendable bridge element. The rigid body has a central hole and the first ring element includes a first hole. Each of the central and first holes can receive a fastener for attaching the bone plate to the bone.

Still referring to the bone plate for the proximal radius, the central hole may be threaded and define a central axis, and the first hole may be threaded and define a first thread axis. The first arm may extend from the rigid body proximal-medially, and the first curved bendable bridge may be attached to the medial edge of the rigid body. The bone plate may also have a second arm extending proximal-laterally from the rigid body and including a second ring element attached to the lateral edge of the rigid body by a second curved bendable bridge element, the second ring element including a second hole having a thread that defines a second thread axis. The bone plate may also have a third arm extending proximally from the rigid body and including a third ring element attached to the proximal end of the rigid body by a third bridge element, the third ring element including a third threaded hole defining a third thread axis. The first, second and third arms form a fork-like structure and the first, second and third thread axes converge but do not intersect. The bone plate may also have a fourth arm extending distally from the rigid body. The fourth arm may have a fourth ring element attached to the distal end of the rigid body, the fourth ring element having a fourth threaded hole defining a fourth thread axis. The bone plate may also have a first, a second, a third and a central drill guide preassembled into the first, second, third and central holes, respectively. Each of the first curved, second curved and third bendable bridge elements is less stiff than the rigid body, but together preferably have a combined stiffness that approximates the stiffness of the rigid body. Each of the first, second and third drill guides is adapted for application of a bending tool, such that a user may use a pair of bending tools to apply a leveraging force to reconfigure any one of the first, second and third arms. The bone plate may also have a fifth arm extending distally from the fourth ring element. The fifth arm may have a fifth ring element attached to the distal end of the rigid body by a fifth bendable bridge element. The fifth ring element may have a fifth threaded hole for receiving a fastener, and have a fifth drill guide preassembled into the fifth hole. Each of the fourth and fifth bendable bridge elements is less stiff than the rigid body, and each of the fourth and fifth drill guides is adapted for application of a bending tool, such that a user may use a pair of bending tools to apply a leveraging force to reconfigure either of the fourth and fifth arms. The fourth and fifth bendable bridge elements may also be fragmentable, such that a user may use the pair of bending tools to apply a leveraging force to fatigue fracture the fourth bendable bridge element in order to remove the fourth and fifth arms, and to apply a leveraging force to fatigue fracture the fifth bendable bridge in order to remove the fifth arm.

According to another aspect of the system, bone plates for the lateral and medial surfaces of the distal humerus each have a rigid body portion with substantially the same thickness. The rigid portion of each of the medial and lateral plates has a distal end, a proximal end, a top surface, a bottom surface, a medial edge and an opposing lateral edge. The plates also have a plurality of holes extending between the top and bottom surfaces, each of the holes for receiving a fastener for attachment of the bone plate to the bone. The lateral plate also has at least one positioning foot extending from an edge downwardly towards the bone surface to aid in the positioning of the bone plate on the bone surface.

Still referring to the bone plate for the lateral and medial surfaces of the distal humerus, the bone plates may also each have a first segment attached to the distal end of the rigid body portion by a first bendable bridge element that is longitudinally aligned along one of the medial and lateral edges of the rigid body portion, and the first segment includes a threaded hole for receiving one of the fasteners. The bone plates may each also have a proximal edge of the first segment, and the proximal edge and the distal end of the rigid body are spaced apart and define a gap, and the gap includes a throat opening adjacent to the first bendable bridge element and is configured for guiding a K-wire passed therethrough. The bone plates may also each have a second segment attached to the distal edge of the first segment by a second bendable bridge element that is longitudinally aligned with the first bendable bridge element, and the second segment includes a threaded hole for receiving one of the fasteners. The bone plates may also each have one or more elongated slot for receiving a compression fastener, and the length of the slot is greater than the width of the slot and the length is oriented in the longitudinal direction of the respective bone plate. The lateral plate includes recesses at the bottom surface of the plate on at least one side, and preferably both sides, of the elongated slot to permit clearance for screw angulation toward the center of the bone for improved purchase of the screws. The thickness of the rigid body portion on respective medial side and lateral sides of the slots may also be thinner than the average thickness of the rigid body portion for each of the medial and lateral plates. The bone plates may also each have an hourglass-shaped opening extending between the top and bottom surfaces, and the hourglass-shaped opening has two ends, each of which are configured to guide a K-wire passed therethrough. The proximal end of each of the bone plates may also be tapered. The thickness of the first bridge element may also be less than the thickness of the rigid body portion. The bone plate may each also have a distal threaded hole near the distal end of the rigid body, a distal tall drill guide preassembled into the distal threaded hole, and a first tall drill guide preassembled into the first threaded hole. The distal and first tall drill guides may be adapted for application of a bending tool, such that a user may use a pair of bending tools to apply a leveraging force to reconfigure the first bendable bridge, thereby repositioning the first segment to a desired orientation with respect to the bone. The bone plate may each also have a plurality of proximal threaded holes located in the rigid body portion near the proximal end, and a like plurality of short drill guides, and each of the proximal threaded holes is preassembled with one of the short drill guides.

According to another aspect of the system, a bone plate for the posterolateral surface of the distal humerus has a body with a thickness substantially greater than the medial plate (greater than fifty percent thicker). The body has a proximal end, a distal end and a curvilinear, longitudinal axis extending therebetween. A first arm and a second arm extend from proximal end on opposing sides of the longitudinal axis, thereby forming a Y-shape, and a third arm extends transversely away from the longitudinal axis to extend partially around the lateral side of the distal humerus. The first, second, and third arms each includes a ring element having a hole and are attached to the body by respective bendable bridge elements. The body includes threaded holes and an elongated slot, each of which may be located along the longitudinal axis. The slot may be configured to receive a compression fastener. Each of threaded holes is configured for receiving one of the fasteners. The threaded holes may be preassembled with a plurality of drill guides, with a proximal hole receiving a short drill guide. In the same manner as with the lateral and medial plates, the surgeon may closely match the shape of posterolateral plate to the bone surface and redirect the trajectories of the fasteners to capture bone fragments and avoid fracture lines and other fasteners.

According to the system, the medial and lateral plates can be used together in a surgical approach that positions the plates in a relatively parallel configuration on opposite sides of the distal humerus bone. Alternatively, the medial and posterolateral plates can be used together in a surgical approach that positions the plates in a relatively orthogonal configuration on the distal humerus bone. In either configuration, the resulting system of plates has substantially similar stiffness on the distal humerus bone.

According to another aspect of the system, a bone plate for the coronoid has a plurality of ring elements including a central ring element, each of the ring elements having a threaded hole for receiving a locking fastener. The bone plate also has a plurality of bendable bridge elements interconnecting the ring elements, and the plurality of ring elements are arranged into a plurality of arms extending radially from the central ring element.

Still referring to the bone plate for the coronoid, the plurality of arms may include a first arm extending distally from the central ring element, a second arm extending medially from the central ring element and a third arm extending laterally from the central ring element. The first arm may have three of the plurality of ring elements spaced apart and arranged linearly, and the second arm may have one of the plurality of ring elements, and the third arm may have one of the plurality of ring elements. The bone plate may also have a buttress element attached to one of the plurality of ring elements by a bendable web element, and the bendable web element is reconfigurable in situ such that the buttress element can bear against the bone surface. The buttress element may extend proximally from the central ring element. The buttress element also may extend medially from the ring element of the second arm. The bone plate may also have a plurality of drill guides, and each of the ring elements is preassembled with one of the drill guides. The drill guides may be removably attachable to a bending tool, such that a user may use a pair of bending tools to apply a leveraging force to reconfigure, in situ, each of the first, second and third arms.

According to another aspect of the system, a bone plate for the olecranon has a body portion having a distal end, a proximal end, a longitudinal axis, a medial edge and a lateral edge. The bone plate also has a head portion transversely positioned on the distal end of the body portion. The bone plate also has a proximal arm extending proximally from the head portion and including a proximal ring element attached to the head portion by a proximal bendable bridge element, such that the proximal arm is reconfigurable in a sagittal plane containing the longitudinal axis and perpendicular to the top surface. The bone plate also has a plurality of threaded holes, and each threaded hole defines a thread axis and can receive a fixed-angle locking fastener for attaching the bone plate to the bone.

Still referring to the bone plate for the olecranon, the proximal ring element may have at least one threaded hole, and the body portion may have a plurality of threaded holes aligned longitudinally, and the head portion may have two threaded holes aligned transversely. The two thread axes of the head portion are transversely offset from the thread axis of the proximal ring element, such that when the proximal arm is reconfigured in the sagittal plane in a direction to result in the thread axis of the proximal ring element to converge with the two thread axes of the head portion, the thread axis of the proximal ring element passes between the two thread axes of the head portion. The bone plate may also have a medial arm extending medially from the body portion and including a medial ring element attached to the medial edge of the body portion by a medial bendable bridge element. The bone plate may also have a lateral arm extending laterally from the body portion (opposite of the medial arm, where provided) and including a lateral ring element attached to the lateral edge of the body portion by a lateral bendable bridge element, and each of the medial and lateral ring elements may have a threaded hole defining a thread axis for receiving a fixed-angle locking fastener. The medial and lateral bridge elements are configured such that the axes through the holes of the medial and lateral ring elements generally converge toward each other, but do not extend within a common plane. The bone plate may also have a plurality of drill guides, wherein each of the threaded holes is preassembled with one of the drill guides. The drill guides may be removably attachable to a bending tool, such that a user may use a pair of bending tools to apply a leveraging force to reconfigure, in situ, each of the medial, lateral and proximal arms. The bone plate may also have a slot in the body portion for receiving a non-locking compression fastener.

According to another aspect of the system, a bone plate has a tapered, threaded hole configured for receiving a fixed-angle, locking fastener having a tapered, threaded head to engage the tapered, threaded hole for attaching the bone plate to the bone, the threaded hole defining a hole axis. The system also has a multidirectional compression fastener for insertion into the tapered, threaded hole for attaching the bone plate to the bone. The multidirectional compression fastener has an elongated shank portion having proximal and distal ends and defining a fastener axis. The multidirectional compression fastener also has a smooth, frustoconically shaped head with a large diameter end and a small diameter end, and the small diameter end is attached to the proximal end of the shank portion, and the large diameter end has a circular, peripheral edge that defines a proximal face with a recess for receiving a driving tool. The multidirectional compression fastener is fully insertable into the tapered, threaded hole, such that the smooth, frustoconically shaped head compresses against the tapered, threaded hole, and the fastener axis and the hole axis define an insertion angle.

Still referring to the multidirectional compression fastener, the elongated shank may be at least partially threaded for engagement into the bone. The insertion angle may range from zero to about 15 degrees and may be contained in any plane containing the hole axis. The circular, peripheral edge may also have an external radius. The smooth, frustoconically shaped head may define an included angle of about 42 degrees centered on the fastener axis. The system may also have a slot extending through the thickness of the bone plate, and the slot is sized and configured to receive a conventional compression screw having a spherical head. The system may also have a washer for receiving the multidirectional compression fastener. The washer has a bore therethrough for receiving the multidirectional compression fastener and an outer surface sized and shaped similarly to the spherical head of the conventional compression screw, such that the multidirectional compression fastener and the washer may be used in combination in the slot in a similar manner as a conventional compression screw to aid in the reduction of the bone fracture and to attach the bone plate to the bone. A portion of the bore of the washer may be conically shaped, such that the proximal face of the multidirectional compression faster is approximately flush with the top of the washer when fully inserted into the washer. In a preferred embodiment, the screw and washer are engageable together such that they may be handled together as a unit during a surgical procedure.

According to another aspect of the system, the system has a bone plate having a threaded hole defining a thread axis for receiving a fixed angle, locking fastener. The system also has a drill guide preassembled into the threaded hole, the drill guide including a drill guide bore sized to guide a bone drill. The system also has an insertion tool having a cylindrical body with distal and proximal ends and a longitudinal axis extending therebetween. The cylindrical body has a grip surface for holding the insertion tool during use. The cylindrical body also has a longitudinal bore extending between the distal and proximal ends and sized for guiding a K-wire, and the distal end is configured to be removably attached to the drill guide so that the longitudinal bore aligns with the thread axis. The distal end of the insertion tool may also fit securely into the drill guide, such that the user may use the cylindrical body as a handle to manipulate the bone plate during the surgical procedure.

BRIEF DESCRIPTION OF THE DRAWINGS

FIG. 3 is a top perspective view of a proximal radius plate;
FIG. 3A is a top perspective of a smaller version of a proximal radius plate;
FIG. 4 is a bottom perspective view of the proximal radius plate of FIG. 3;
FIG. 5 is a perspective view of a pair of bending tools as they may be applied in situ to reconfigure the proximal radius plate of FIG. 3;
FIG. 6 is perspective view of the bending tools of FIG. 5 as they may be alternately applied in situ to reconfigure the proximal radius plate of FIG. 3;
FIG. 7 is a bottom perspective view of the proximal radius plate of FIG. 3 with a plurality of fasteners fully inserted;
FIG. 9 is a top, medial perspective view of a lateral plate for the distal humerus;
FIG. 10 is a top, lateral perspective view of the lateral plate of FIG. 9;
FIG. 11 is a bottom perspective view of the lateral plate of FIG. 9;
FIG. 15A is a top perspective view of a posterolateral plate for the distal humerus;
FIG. 15B is a bottom perspective view of the posterolateral plate of FIG. 15A;
FIG. 16 is top perspective view of the posterolateral plate of FIG. 15A, shown preassembled with a plurality of first drill guides;
FIG. 17 is top perspective view of the posterolateral plate of FIG. 15A, shown with a plurality of fasteners fully inserted;
FIG. 23A is a top perspective view of an olecranon plate;
FIG. 23B is a bottom perspective view of the olecranon plate of FIG. 23A;
FIG. 23C is a bottom perspective view of the olecranon plate of FIG. 23A, including a plurality of fasteners fully inserted;
FIG. 27 is a head end view of a conventional compression screw;
FIG. 28 is a side view of the compression screw of FIG. 27;
FIG. 29 is a head end view of a multidirectional locking screw;
FIG. 30 is a side view of the multidirectional locking screw of FIG. 29;
FIG. 31 is a cross-sectional view of the multidirectional locking screw of FIG. 29 inserted into a threaded hole of a bone plate;
FIG. 32 is a perspective view of a fixed-angle locking screw;
FIG. 33 is a head end view of the fixed-angle locking screw of FIG. 32;

FIG. 34 is a detailed cross-sectional view of the proximal portion of the fixed-angle locking screw of FIG. 32;

FIG. 41 is a perspective view of a first drill guide that may be preassembled into a tapered, threaded hole of a bone plate;

FIG. 42 is another perspective view of the first drill guide shown in FIG. 41;

FIG. 43 is a perspective view of a second drill guide that may be preassembled into a tapered, threaded hole of a bone plate;

FIG. 44 is another perspective view of the second drill guide shown in FIG. 43;

FIG. 45 is a perspective view of the first drill guide of FIG. 41 and the second drill guide of FIG. 43 preassembled into the distal portion of a bone plate shown;

Among those benefits and improvements that have been disclosed, other advantages of the devices and methods described herein will become apparent from the following description taken in conjunction with the accompanying figures. The figures constitute a part of this specification and include illustrative embodiments of the claimed invention.

DETAILED DESCRIPTION OF THE PREFERRED EMBODIMENTS

Figure 1:
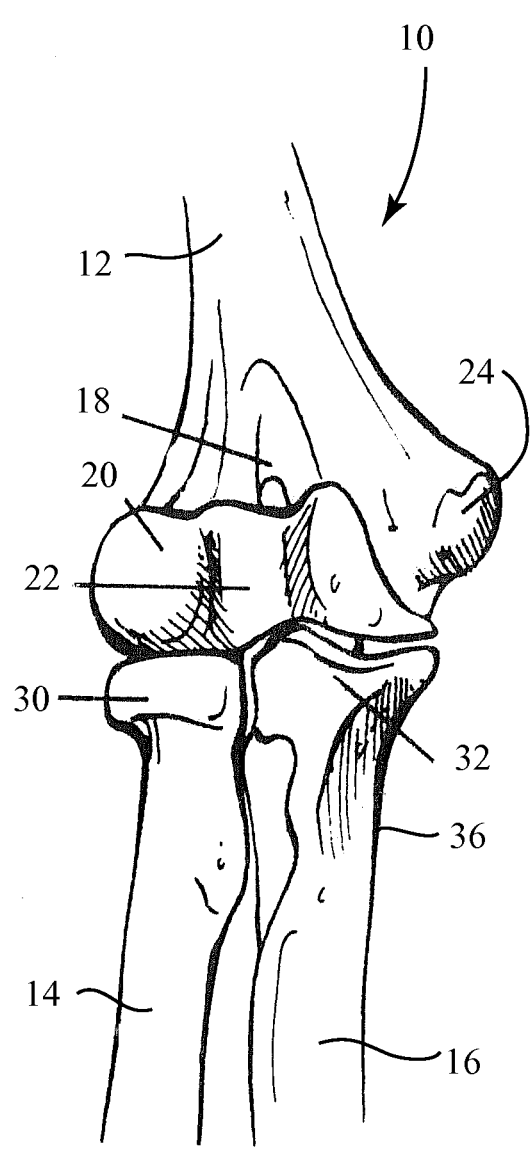
FIG. 1 is an anterior (front) view of the bones of the human elbow joint.
Figure 2:
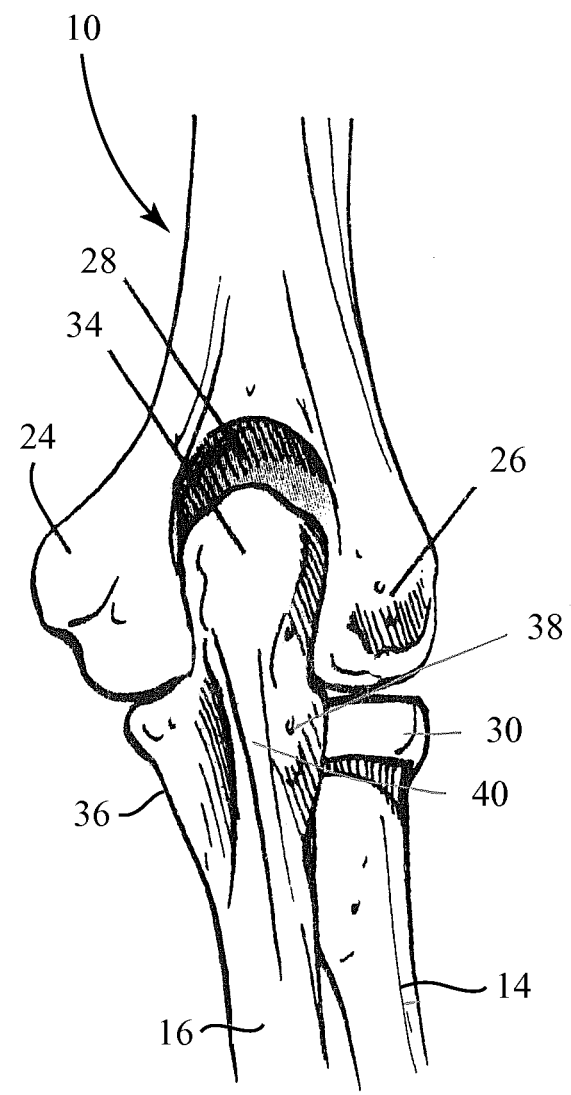
FIG. 2 is a posterior (back) view of the bones of the human elbow joint.

FIG. 1 is an anterior (front) view and FIG. 2 is a posterior (back) view of the bones of the human elbow joint 10: the distal humerus 12, the proximal radius 14 and the proximal ulna 16. The distal humerus 12 includes the coronoid fossa 18, the capitellum 20, the trochlea 22, the medial epicondyle 24 and the lateral epicondyle 26, and the olecranon fossa 28 therebetween. The proximal radius 14 includes the radial head 30. The proximal ulna 16 includes the coronoid process 32 (FIG. 1) and the olecranon 34 (FIG. 2) which articulates within the olecranon fossa 28 between the lateral and medial epicondyles 24, 26 of distal humerus 12. Each of the distal humerus 12, proximal radius 14 and proximal ulna 16 are susceptible to a large variety of fractures, such as during a fall.

The present system for the repair of elbow fractures may include a plurality of anatomically specific bone plates and a plurality of fasteners for the attachment of the plates to the bone. The system may include a proximal radius plate for repair of the proximal radius. The system may also include a lateral plate, a medial plate and a posterolateral plate for repair of the distal humerus. The system may further include an olecranon plate and a coronoid plate for the repair of the proximal ulna.

Although each of the bone plates of the system described herein are designed to fit closely to specific bone surfaces of the elbow joint, the plates share numerous advantages compared to conventional plates. For example, each of the plates has portions that are reconfigurable in situ, such that the surgeon may alter the bone plate shape while it is positioned on the bone to more closely fit and support the bone surface. This also allows the surgeon to redirect the trajectories of the fasteners if necessary to capture bone fragments or to avoid intersecting other fastener trajectories.

To facilitate in situ reconfiguration of the plate using bending tools, as well as to facilitate hole drilling for rapid insertion of bone fasteners, each of the plates described herein may be preassembled with a plurality of drill guides, such as either of a first drill guide 1400 shown in FIG. 41, a second drill guide 1500 shown in FIG. 43, or a combination thereof.

Each of the plates of the present system may be formed from any one of numerous materials known in the art, including a stainless steel, a titanium and a titanium alloy such as Ti-6Al-4V. Each of the plates is preferably machined from a solid round bar of Ti-6Al-4V-ELI in the fully annealed condition. Each plate is machined to its respective anatomical shape, described below, to ensure minimal or no work hardening. After machining, the parts are polished and anodized. The resulting plate material is finished fully 'soft' with minimal or no work hardening to and enable in situ shaping without fracture of the plate, as described in detail below. In general, each of the plates described herein are significantly thinner than currently available plates for the same types of fractures, yet still has the appropriate stiffness to support the respective fractured bone. In addition, each of the fasteners provided to attach the bone plates to the bone described herein (FIGS. 28 through 38) has a low profile design, i.e., the head of each fastener is configured to seat relatively flush to the top surface of the plate, thereby minimizing trauma to surrounding soft tissues.

Figure 35:
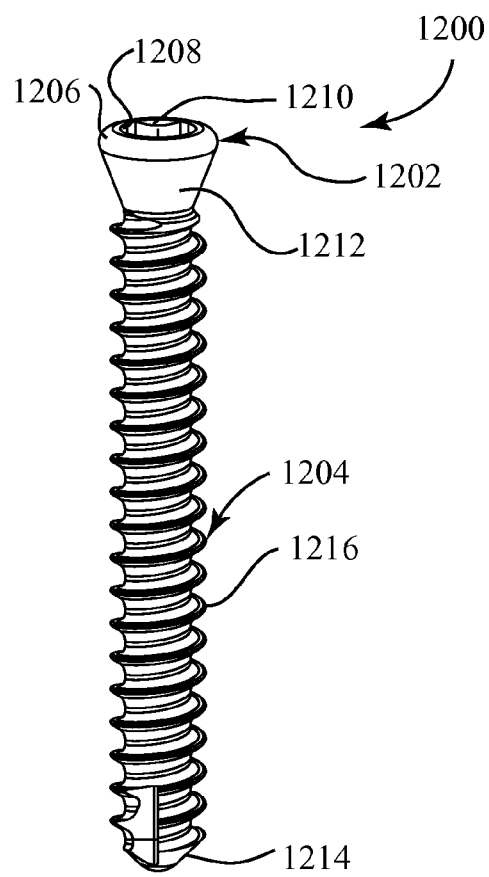
FIG. 35 is a perspective view of a multidirectional compression screw.
Figure 39:
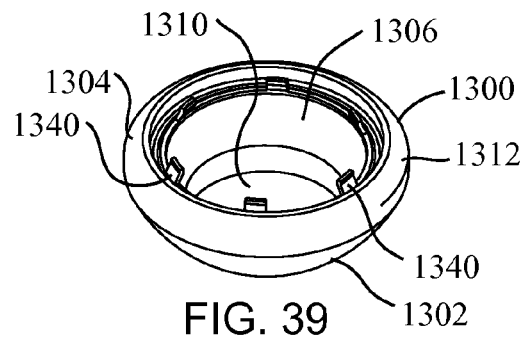
FIG. 39 is a perspective view of a washer for use with the multidirectional compression screw of FIG. 35.
Figure 40:
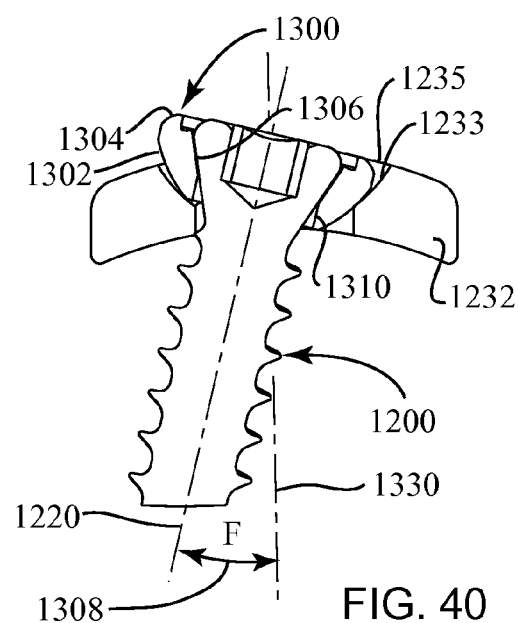
FIG. 40 is a cross-sectional view of the washer and multidirectional compression screw of FIG. 39 assembled into a slot of a bone plate at an insertion angle F.

Each of the bone plates of the present system include a plurality of holes, wherein each hole may be configured to receive any one of the bone fastener embodiments shown in FIGS. 28 through 40, including a standard compression screw 700 shown in FIG. 28, a fixed-angle locking screw 1100 shown in FIG. 32, a multidirectional locking screw 1000 shown in FIG. 30, a multidirectional compression screw 1200 shown in FIG. 35, and a multidirectional compression screw 1200 with washer 1300 shown in FIG. 40. Each of the plates of the present system includes at least one hole for receiving a locking fastener, such as either of fixed-angle locking screw 1100 and multidirectional locking screw 1000.

Those skilled in the art will recognize that although the bone plates are described for specific elbow fracture applications, each of the bone plates, fasteners, instruments and methods described herein may be easily modified for application to other bones and other types of bone fractures.

Bone Plate for the Proximal Radius

FIG. 3 is a perspective view of a top surface 101 and FIG. 4 is a perspective view of a bottom surface 103 of a bone plate 100 for the proximal radius, also called radial plate 100. Radial plate 100 has a rigid body 102 with a proximal end 104, a distal end 106, a top surface 101, a bottom surface 103 defining longitudinal axis 108 having a convex proximal portion. Rigid body 102 has a medial edge 110 and a lateral edge 112. Radial plate 100 may be symmetrically shaped as shown in FIG. 3, such that it may be used on either of the right and left elbows, as described in more detail below. Rigid body 102 also includes a first central hole 176 and a second central hole 186, each extending between the top surface 101 and the bottom surface 103, for receiving a bone fastener for attaching radial plate 100 to the bone. A first arm 120 extends proximal-medially from rigid body 102 and includes a first ring element 122 and a first bendable bridge element 124 attached to medial edge 110 of rigid body 102. Ring element 122 has a first hole 126 for receiving a bone fastener. First bendable bridge element 124 is curved so that first arm 120 extends initially from rigid body 102 in the medial direction, and then finally in the proximal direction. The amount of curvature shown in FIGS. 3 and 4 of first arm 120 is approximately 90 degrees and not within a single plane, although the curvature may vary. The width across the first arm at B1 is less than the width across the first arm at B2.

As shown in FIGS. 3 and 4, radial plate 100 may also include a second arm 130 extending proximal-laterally. Second arm 130 includes a second ring element 132 attached to lateral edge 112 of rigid body 102 by a second bendable bridge element 134, which is also curved and opposing first bendable bridge element 124. As shown, second arm 130 may be, but is not necessarily, a mirror image of first arm 120. The width across the second arm at B3 is less than the width across the second arm at B4. Second ring element 132 includes a second hole 136 for receiving a bone fastener.

Radial plate 100 may also include a third arm 140 extending proximally from rigid body 102 and between first arm 120 and second arm 130. Third arm 140 includes a third ring element 142 attached to proximal end 104 of rigid body 102 by a third bridge element 144 having a third hole 146 for receiving a bone fastener. Each of the first, second and third arms 120, 130, 140 is less stiff than the rigid body 110, but together have a combined stiffness that approximates (within 20%, and more preferably ±10%) the stiffness of the rigid body. First, second and third arms 120, 130 and 140, respectively, are spaced apart to form an out-of-plane fork-like (preferably trident) shape, thereby allowing visualization of the bone surface there beneath.

Figure 8:
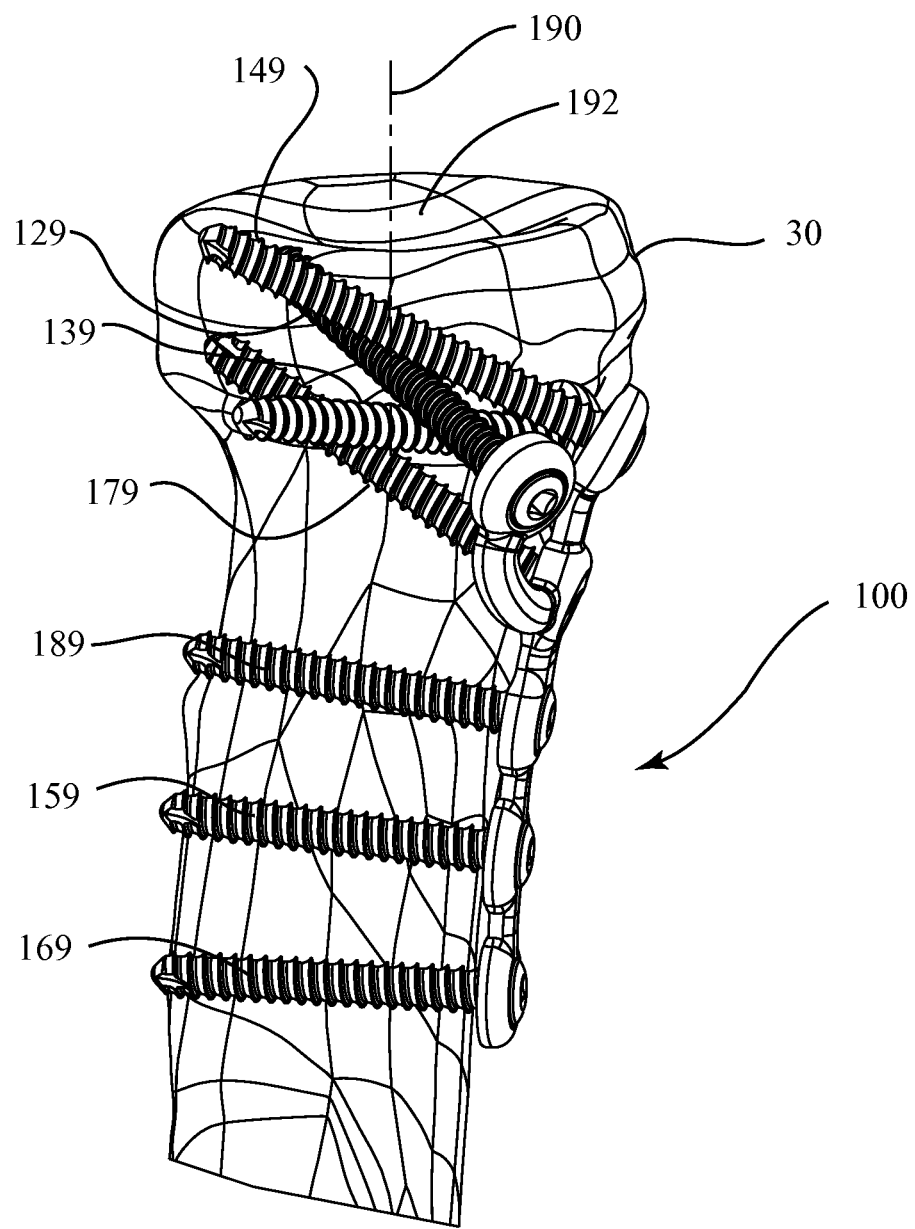
FIG. 8 is a wire frame, lateral view of the proximal radius plate of FIG. 3 attached with a plurality of fasteners to the proximal radius.

Referring to FIGS. 4, 7 and 8, the first, second and third rings 122, 132, and 142 are preferably relatively situated so as to be positioned approximately about the exterior of an imaginary sphere. This adapts the rings 122, 132, 142 for seating on the metaphyseal surface of the proximal radius, which is generally cylindrically curved in the medial-lateral direction and convex in the longitudinal direction, at least at the proximal end in a manner which approximates a spherical shape. As formed, the axes 127, 137 and 147 of the holes 126, 136 and 146 criss-cross through a common central axis 190 which aligns with the predicted center of the articular surface 192 of the proximal radius 30 for which the proximal radius plate 100 is sized. When the plate is designed for use on larger radius bones, the central axis 190 along which the holes axes 127, 137, 147 criss-cross will be further from the plate, and when the plate is design for use on smaller radius bones, the central axis 190 along which the hole axes 127, 137, 147 criss-cross will be closer to the plate.

For example, FIG. 3A illustrates a radial plate 100a scaled down in size relative to radial plate 100 to accommodate smaller radius bones. The bridge elements 124a, 134a, and 144a are differently oriented relative to bridge elements 124, 134, 144 so as to configure the rings 122a, 132a, 142a to define a smaller radius of curvature therebetween so that the rings are adapted to seat on a smaller proximal radial head. The axes through the holes in the rings criss-cross closer to the plate.

Referring back to FIGS. 3, 4 and 7, as will be described further below, each of the first, second and third arms 120, 130 and 140, respectively, may be individually reconfigured, as necessary, by the surgeon to fit the bone surface and to change the trajectories of fasteners inserted through the rings of such arms.

Radial plate 100 may also include a fourth arm 150 extending distally from rigid body 102 along longitudinal axis 108. Fourth arm 150 includes a fourth ring element 152 having a fourth hole 156 and connected to distal end 106 of rigid body 102 by a fourth bendable bridge element 154.

Radial plate 100 may also include a fifth arm 160 extending distally from fourth ring element 152. Fifth arm 160 includes a fifth ring element 162 having a fifth hole 166 and attached to fourth ring element 152 by a fifth bendable bridge 164.

Each of first, second, third, fourth, fifth, first central and second central holes 126, 136, 146, 156, 166, 176 and 186, respectively, is preferably taper threaded to receive any one of multidirectional locking screw 1000, fixed-angle locking screw 1100, and multidirectional compression screw 1200.

Still referring to FIGS. 3 and 4, a plurality of drill guides may be preassembled to radial plate 100 to facilitate drilling fastener holes into the bone and to provide instrumentation attachment points for reconfiguring radial plate 100 during the surgical procedure. Each of first, second, third, fourth, fifth, first central and second central holes 126, 136, 146, 156, 166, 176 and 186, respectively, may be configured, such as with a tapered thread, to receive a first, second, third, fourth, fifth, first central and second central drill guide, 128, 138, 148, 158, 168, 178 and 188, respectively, each of which is preferably first drill guide 1400 (FIG. 41).

Each of bendable bridges 124, 134, 144, 154 and 164 are significantly less resistant to bending and twisting than rigid body 102 and, therefore, individually reconfigurable with the appropriate tools, as now described. FIG. 5 is a perspective view of a pair of bending tools 2160, 2180 as they may be applied in situ to reconfigure fourth arm 150 of radial plate 100. FIG. 6 is a perspective view of bending tools 2160, 2180 as they may be applied in situ to reconfigure first arm 120 of radial plate 100. Bending tool 2160 is formed into an L-shape from a metal rod, wherein one longer portion of the L-shape comprises a handle 2166 and the other shorter portion comprises an arm 2168. A first end effector 2162 is attached to the free end of handle 2166 and a second end effector 2164 is attached to the free end of arm 2168. Each of first and second end effectors 2162, 2164 may be securely yet removably attached to any one of drill guides 128, 138, 148, 158, 168, 178 and 188 (FIG. 3), as shown in FIGS. 5 and 6. Bending tool 2180 is also formed into an L-shape from a metal rod, wherein one longer portion of the L-shape comprises a handle 2186 and the other shorter portion comprises an arm 2188. A first end effector 2182 is attached to the free end of handle 2186 and a second end effector 2184 is attached to the free end of arm 2188. Each of first and second end effectors of either of tools 2860, 2180 may be securely yet removably attached to any one of drill guides 128, 138, 148, 158, 168, 178 and 188 (FIG. 3), as shown in FIGS. 5 and 6.

An x-y-z coordinate system is shown in each of FIGS. 5 and 6. The x-y plane approximately corresponds to the medial-lateral direction and the x-z direction approximately corresponds to the anterior-posterior direction with respect to the surface of the proximal radius.

FIG. 5 shows how bending tools 2160, 2180 may be attached to bend bridges 154, 164 in the x-z plane by applying the leveraging force in the direction of arrows 2192, or to be also used to twist bridges 154, 164 about the x-axis by applying the leveraging force in the direction of the arrows 2190. Generally, equal but oppositely directed forces may be applied to each of the bending tools 2160, 2180 to generate the leveraging force or couple. In this way, radial plate 100 may be reconfigured in situ to closely match the shape of the proximal radius surface. This also allows the surgeon to redirect the axes of holes 156, 166 into a desired direction, such as to capture a bone fragment or to avoid a fracture line or fastener already inserted into the bone.

FIG. 6 shows how bending tools 2160, 2180 may be used to twist first arm 120 in the y-z plane by applying the leveraging force in the direction of the arrows 2194, or to twist first arm 120 in the x-z plane by applying the leveraging force in the direction of the arrows 2196, such that ring element 122 fits closely against the proximal radius surface. Because first arm 120 has a curvature of about 90 degrees and because the arm is narrower at B1 than at B2, the arm 120 is structurally adapted to sweep in a predictable manner (the twisting of arm will be at or adjacent B1) so as to minimize interaction between axis 137 and the other axes. Similarly, second arm 130 may also be reconfigured. Radial plate 100 is provided to the user with a configuration that closely matches the majority of patients and with fastener trajectories (thread axes) that do not intersect. However, using bending tools 2160 and 2180 allows fine, in situ adjustments to improve the quality of the internal fixation. The surgeon may quickly and safely make a reasonable number of small adjustments to the plate configuration without the danger of microcrack formation that may lead to fracture after implantation. A bendable plate (albeit of different configuration, structure and function), and the in situ use thereof, and a pair of dedicated bending tools for in situ bending of the plate are disclosed in co-owned U.S. Pub. No. 20060161158A1, 20070233111A1, and 20070233112A1, all of which are hereby incorporated by reference herein in their entireties.

When radial plate 100 is placed on the radial head 30 (FIGS. 1 and 2), either the first or second ring elements 122, 132 of the first and second arms 120, 130 will generally be slightly spaced from the surface of the bone. The spaced apart ring will be the ring located at the lateral side of the radius bone. This configuration of the radial plate 100 allows a single 'ambidextrous' radius plate to be used on either left or right radius bones in closest possible conformation to each such bone. The spaced apart ring may be repositioned, if desired, to seat closer to the bone by the use of the bending tools.

FIG. 7 is a perspective view of bottom surface 103 of radial plate 100 with a plurality of fasteners fully inserted, including fasteners 129, 139, 149, 159, 169, 179 and 189 into holes 126, 136, 146, 156, 166, 176 and 186, respectively. FIG. 8 shows the radial plate 100 attached to the proximal radius. A plurality of fasteners 129, 139, 149 and 179 form an interdigitating, rigid scaffold beneath the articular surface of the radial head.

Holes 126, 136, 146 and 176 correspond to thread axes 127, 137, 147 and 177, respectively, which may be provided in an interdigitating arrangement, such that thread axis 127 passes between axes 137 and 177, and thread axis 137 passes between axes 147 and 127. Stated another way, axes 127, 137, 147 and 177 are all distally directed relative to the bottom surface 103 of the radius plate 100, with axis 147 being distalmost, axis 177 being proximalmost and extending toward a common point with axis 147, and axes 127 and 137 extending transverse to each other (76°±6° relative to each other in the medial-lateral direction) and between axes 147 and 177. Due to the curved non-planar shape of first arm 120, when the leveraging force is applied in the direction indicated by arrows 194 in FIG. 6, first arm 120 is biased to bend in the y-z plane, such that axis 127 may be redirected yet remain between axis 137 and 177, and the corresponding fastener trajectories do not intersect. Second arm 130 is biased to bend in a similar manner, such that axis 137 will not intersect either of axes 147 and 127. This interdigitating arrangement provides a strong, load-sharing scaffold while facilitating rapid attachment of radial plate 100 to the bone since hole re-drilling is minimized. If any of the arms 120, 130, 140 are twisted or bent by the surgeon, it is important that the axes 127, 137, 147, and 177 continue to interdigitate, and not conflict.

As shown in FIG. 8, fasteners 129, 139, 149 and 179 may span the proximal radius, such that the fastener tips anchor into cortical bone on the side of the bone opposite radial plate 100. A common fracture location is at the neck of the proximal radius head. Fastener 179 is specifically intended to travel across the neck and span the fracture. This arrangement, together with the use of locking fasteners, provide an exceptionally robust scaffold for supporting the articular surface of the proximal radius. In addition, fasteners 159, 169 and 189 extend diametrically across the diaphysis of the radius bone. These fasteners carry the load on the plate back to the diaphysis. Fourth arm 150 and fifth arm 160 optionally can be removed, by reverse bending, if not required to support the fracture.

While it is not necessary to include all of the above described features in the radial plate 100, all such features are included in a preferred embodiment, as such are considered optimum for configuring the plate to the proximal radius and for supporting fractures thereat.

Bone Plates for the Lateral and Medial Surfaces of the Distal Humerus

FIGS. 9, 10 and 11 show a bone plate for the lateral surface of the distal humerus. FIG. 9 is a perspective view of a top surface 208 and an anterior edge 248 of a lateral plate 200 for the distal humerus. FIG. 10 is a perspective view of the top surface 208 and a posterior edge 250 of lateral plate 200. FIG. 11 is a perspective view of a bottom surface 210 of lateral plate 200. Lateral plate 200 includes a body 206 having a distal end 204, a proximal end 202 and a curvilinear axis 209. The bottom surface 210 at the distal end 204 is concave along the longitudinal axis 209, while the remainder of the bottom surface is flat or convex long the axis. This permits the distal end 204 to seat close to the lateral epicondyle 26. A first locating foot 242 and a second locating foot 244 extend downwardly (toward the bone surface) from posterior edge 250 and are provided to assist the surgeon during placement of lateral plate 200 onto the bone surface by seating on the bone contours of the posterior surface of the distal humerus. Each locating foot 242, 244 has a size (bone contacting surface area) preferably approximating the cross-sectional area of a screw hole (220, 222, 224, 226, 228, 230, 232, discussed below).

Lateral plate 200 may also include a first segment 212 extending along curvilinear axis 209 from distal end 204 of body 206. First segment 212 is attached to distal end 204 by a first bendable bridge element 216, which is offset from curvilinear axis 209 such that it forms a continuation of the posterior edge 250. Lateral plate 200 may further include a second segment 214 extending along curvilinear axis 209 and attached to first segment 212 by a second bendable bridge element 218, which also is offset from curvilinear axis 209 and forms a continuation of the posterior edge 250. First and second bendable bridge elements 216, 218 form a bendable spine 231 that is reconfigurable during the surgical procedure, as will be described. The bendable bridge elements 216, 218 are defined along the posterior edge 250, rather than centrally located, so that when the patient's elbow is placed on a surface, the area of the plate which loads against the surface is smooth so as to prevent discomfort to the patient. The distal end 204 of body 206, segment 212, and segment 214 each have squared off ends opposite the bendable spine 231. This facilitates use of bending tools 1600A, 1600B, as described below with respect to FIGS. 46-48C.

In the present embodiment, body 206 includes first, second, third, fourth, and fifth holes 220, 222, 224, 226 and 228, respectively, each for receiving a fastener. Each of first and second segments, 212 and 214, also include a hole 230 and 232, respectively, for receiving a fastener. Holes 220, 222, 224, 226, 228, 230 and 232 preferably have a tapered thread for receiving any one of multidirectional locking screw 1000, fixed-angle locking screw 1100, and multidirectional compression screw 1200, and also for receiving either one of first drill guide 1400 (FIG. 41) or second drill guide 1500 (FIG. 43). As described for radial plate 100, the use of preassembled drill guides in segments 212 and 214 allows the surgeon to use bending tools to reconfigure bendable spine 231, as will be described for FIGS. 47 and 48. The use of preassembled drill guides in holes 220, 222, 224, 226, 228 permits additional reconfiguration of the plate. The use of preassembled drill guides in any of the threaded holes aids in drilling through the bone in alignment with the holes in the plate, as well as temporary fixation of the plate to the bone with K-wires, as described below.

Lateral plate 200 may also include two elongated slots 234, 236 located in body portion 206 for receiving a compression screw such as either of standard compression screw 700 (FIG. 27) or multidirectional compression screw 1200 (FIG. 40). As it is well-known in the art, the compression fastener may be inserted into slots 234, 236 to dynamically compress lateral plate 200 in the vertical and axial directions to facilitate fracture reduction prior to insertion of the remaining fasteners.

Lateral plate 200 may also include cut-outs 246a, 246b on each side of elongated slot 234 and cut-outs 247a, 247b on each side of elongated slot 236 in order to (i) provide clearance at the edges of the plate for fasteners that are angled toward the posterior of the bone in order to attain maximum purchase on the bone, (ii) to normalize the stiffness on both sides of the slot, (iii) to reduce the stiffness of the plate at a slot to permit bending through a slot via the use of drill guides inserted into threaded holes on either side of a slot and appropriate bending tools, and/or (iv) to make that portion of body 206 less stiff than the adjoining portions, thereby allowing slight reconfiguration of body portion 206 to more closely match the shape of the bone surface upon insertion of a compression fastener. Increased clearance is preferred at the posterior edge 248 of the plate adjacent slots 234, 236, as this is the side toward which the fasteners are angled for bone purchase. It is further preferred that the elongated slots 234, 236 be centered off-axis from longitudinal axis 209, but oriented parallel thereto so as to define two rails of different width connecting the portions of the plate on either side of the slot 234. With respect to slot 234 (slot 236 is similarly structured), larger cut-out 246a is provided in association with larger rail 249a, and smaller cut-out 246b is provided in association with smaller rail 249b. This configuration provides additional clearance at the posterior edge for screw orientation into cortical bone. The area of the cut-outs 246a, 246b are preferably dimensioned such that each of the rails 249a, 249b has substantially equal stiffness (preferably within ten percent of each other, and more preferably within five percent of each other). However, the overall stiffness of the plate body in the region of the slot is reduced by the cut-outs to facilitate reconfiguration of the plate.

Lateral plate 200 may also include an hourglass-shaped openings 238, 239 near distal end 204. Opening 238 reduces the stiffness of the plate between holes 224, 226 to allow distal end 204 to be reconfigurable using bending tools such as shown in FIG. 5 without a discontinuation of posterior and anterior edges 248, 250. The opposing ends of opening 238 may also be configured to guide a conventional K-wire to capture and hold bone fragments while adjacent fasteners are inserted. Opening 239 functions between holes 226 and 228 in the same manner as opening 238. Similarly, each of the spacings 213, 215 between segments 212 and 214 and between segment 212 and distal end 204, respectively, may also be configured to guide a conventional K-wire. To that end, spacings 213, 215 may be shaped to retain a guidewire between a narrower central portion 213a, 215a and a larger closed end 213b, 215b (throat) (FIG. 9). Lateral plate 200 (as well as medial plate 300 or posterolateral plate 400) may optionally include one or more multifunctional hole that may be used to guide a conventional K-wire and as an attachment point for a suture. Such a multifunctional hole is described in detail in U.S. Pub. No. 20070270849A1, which is hereby incorporated by reference herein in its entirety.

It is an important feature of the lateral plate that it is, overall, progressively stiffer from the distal end to the proximal end, corresponding to the loads experienced at respective portions of the plate. The lateral plate is most preferably approximately 2 mm thick along its length and used in conjunction with a medial plate 300, described below, of substantially the same thickness.

While it is not necessary to include all of the above described features in the lateral plate 200, all such features can be included in an embodiment, and the inclusion of the described features is considered optimum for configuring the plate to the lateral surface of the distal humerus and for supporting fractures thereat.

Figure 12:
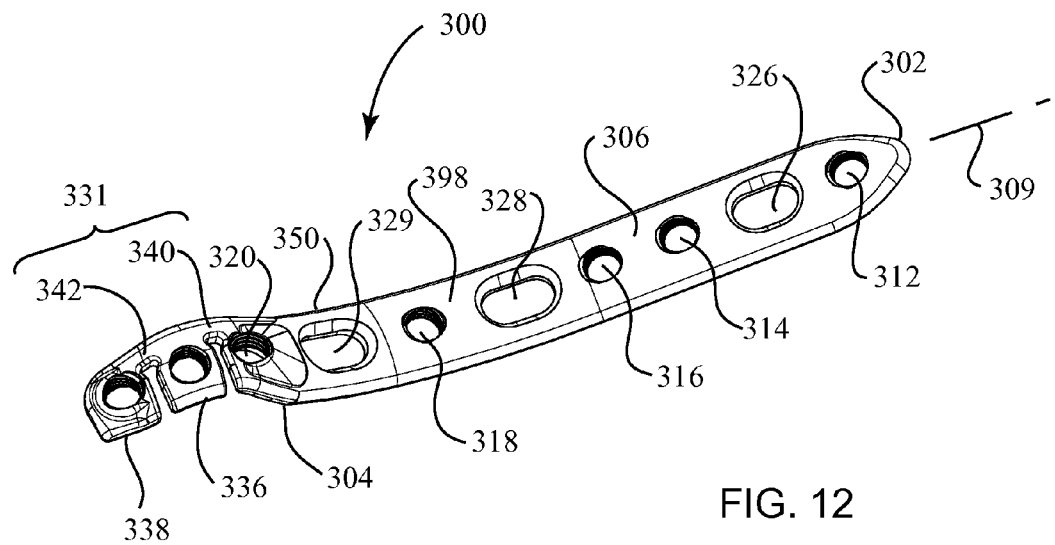
FIG. 12 is a top perspective view of a medial plate for the distal humerus.
Figure 13:
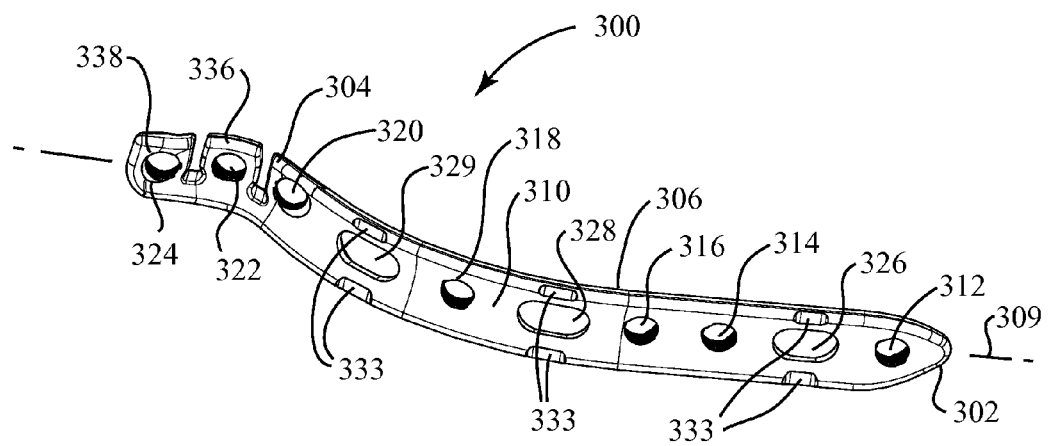
FIG. 13 is a bottom perspective view of the medial plate of FIG. 12.

FIG. 12 is a perspective view of a top surface 398 of a bone plate 300 for the medial surface of the distal humerus, also called a medial plate 300. FIG. 13 is a perspective view of a bottom surface 310 medial plate 300. Medial plate 300 is similar to lateral plate 200, with variations in shape, size, and hole configuration.

Medial plate 300 includes a body 306 having a proximal end 302, a distal end 304 and a curvilinear axis 309. The bottom surface 310 at the distal end 304 is concave along the curvilinear axis 309, while the remainder of the bottom surface is slightly convex or flat along the axis. This permits the distal end 304 to seat close to the medial epicondyle 24. Medial plate 300 also includes a first segment 336 extending along curvilinear axis 309 from distal end 304 of body 306. First segment 336 is attached to distal end 304 by a first bendable bridge element 340, which is offset from curvilinear axis 309, such that it forms a continuation of a posterior edge 350. Medial plate 300 may further include a second segment 338 extending along curvilinear axis 309 and attached to first segment 336 by a second bendable bridge element 342, which also is offset from curvilinear axis 309 and forms a continuation of the posterior edge 350. First and second bridge elements 340, 350 preferably have a portion of reduced thickness (transverse to the axis 309 and width of the plate, and seen in FIG. 13), that facilitates bending thereof. First and second bendable bridge elements 340, 342 form a bendable spine 331 that is reconfigurable during the surgical procedure, as will be described for FIGS. 47 and 48. The distal end 304 of the body 306, segment 336 and segment 338 each have squared off ends opposite the bendable spine 331. This facilitates use of bending tools 1600A, 1600B, as described below with respect to FIGS. 46-48C. The bendable bridge elements 340, 342 are defined along the posterior edge 350, rather than centrally located, so that when the patient's elbow is placed on a surface, the area of the plate which loads against the surface is smooth so as to prevent discomfort to the patient.

Figure 46:
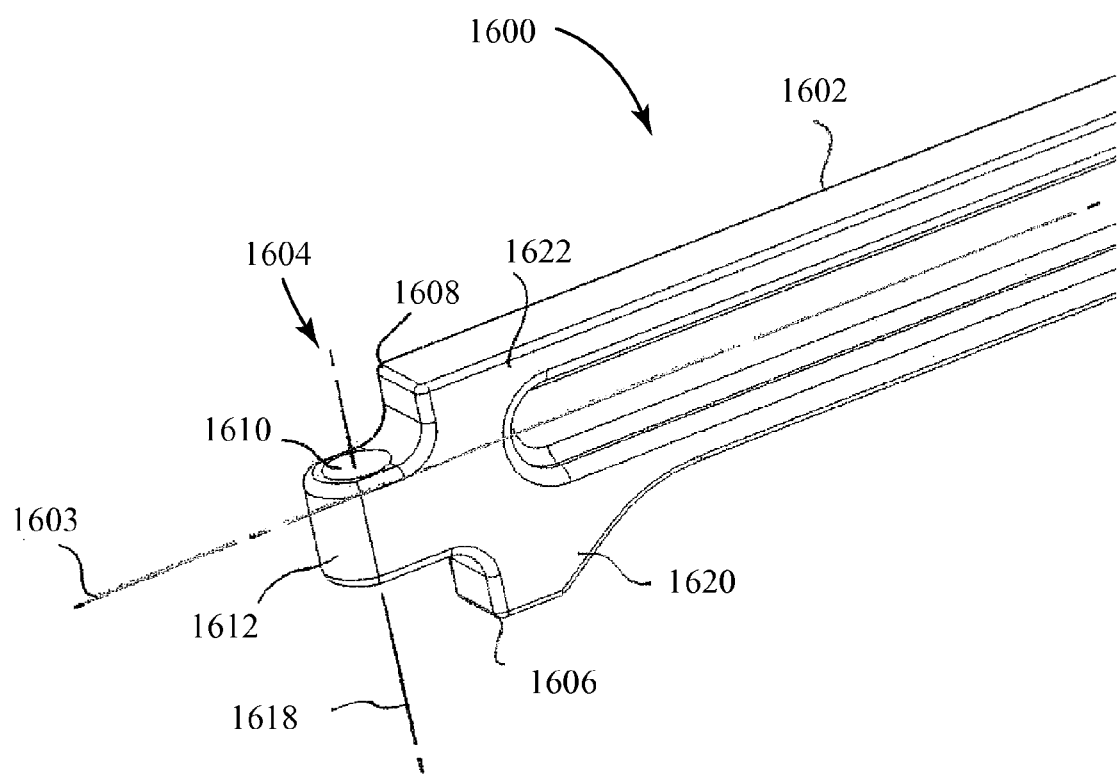
FIG. 46 is a perspective view of a distal portion of a first embodiment of a bending tool.
Figure 47:
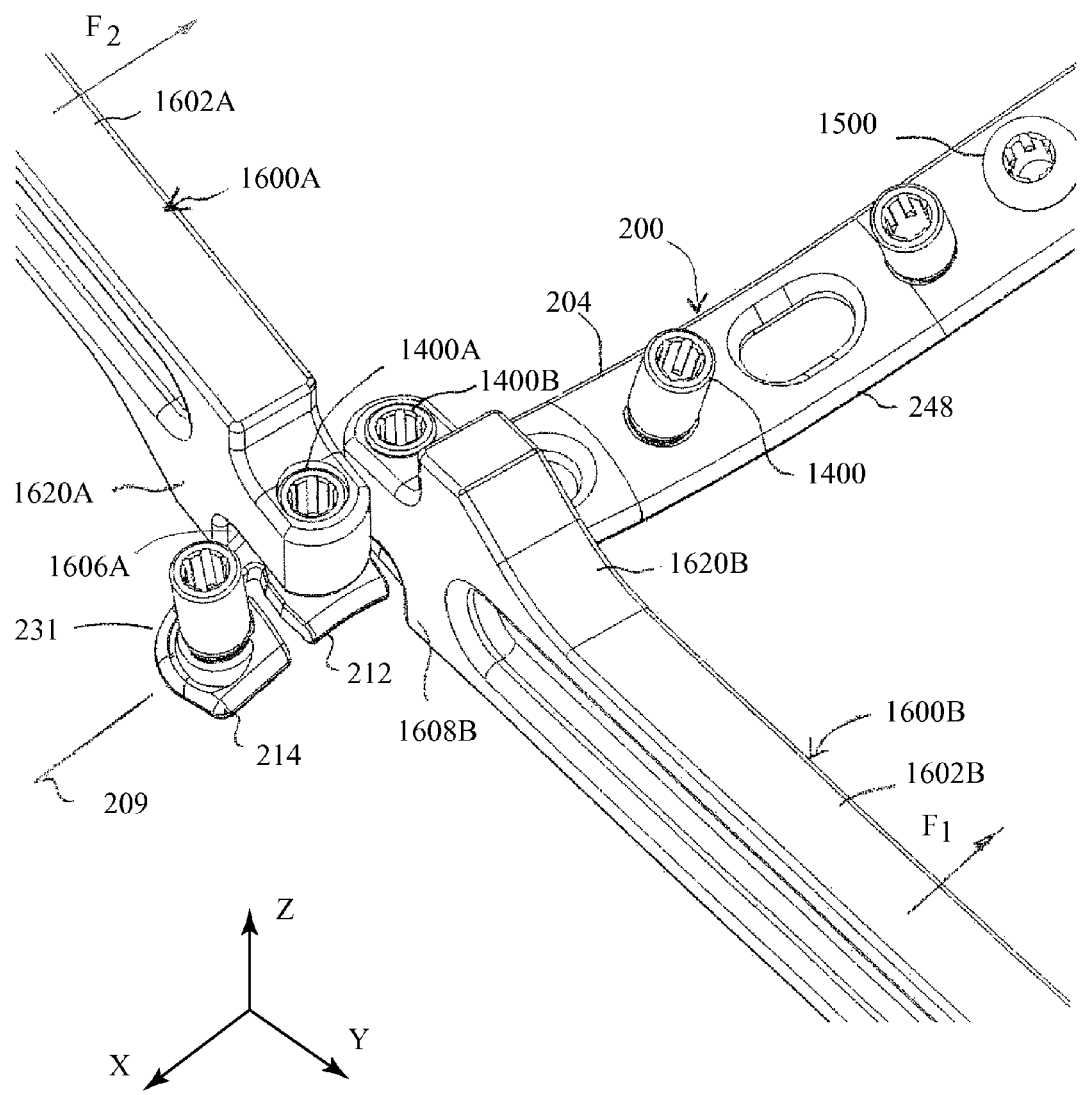
FIG. 47 is a perspective view of a first embodiment of a pair of the bending tools shown in FIG. 46 as they may be used to reconfigure the bone plate shown in FIG. 48 in an x-y plane.

As shown in FIG. 12, body 306 includes first, second, third, fourth and fifth holes, 312, 314, 316, 318 and 320, respectively, each for receiving a fastener. Each of the first and second segments 336 and 338 also include a hole 322 and 324, respectively, for receiving a fastener. Holes 312, 314, 316, 318, 320, 336 and 338 are preferably configured with a tapered thread to receive any one of multidirectional locking screw 1000, fixed-angle locking screw 1100 or multidirectional compression screw 1200, and either one of first drill guide 1400 and second drill guide 1500. As described for radial plate 100, the use of preassembled drill guides in segments 322 and 324 allows the surgeon to use bending tools such as shown in FIGS. 46 and 47 to reconfigure bendable spine 331.

Medial plate 300 may also include a first elongated slot 326, a second elongated slot 328, and a third elongate slot 329, each located in body portion 306 for receiving either one of standard compression screw 700 (FIG. 27) and multidirectional compression screw 1200 (FIG. 40) to facilitate the dynamic compression of medial plate 300 to the bone prior to insertion of the remaining fasteners.

Medial plate 300 may also include a cut-out 333 on each side of each of elongated slots 326, 328 and 329 in order to make that portion of body 306 less stiff than the adjoining portions, thereby allowing slight reconfiguration of body portion 306 to more closely match the shape of the bone surface. For example, (i) drill guides assembled in threaded holes 312, 314, 316, 318, 320 on opposite sides of slots 326, 328, 329 may be subject to force with tools to reconfigure the plate about the slot, and (ii) standard compression screw 700 may be inserted into each of slots 326 and 328 and tightened in order to draw bottom surface 310 against the bone, prior to insertion of the remaining fasteners.

It is an important feature of the medial plate that it is, overall, progressively stiffer from the distal end to the proximal end, corresponding to the loads experienced at respective portions of the plate.

While it is not necessary to include all of the above described features in the medial plate 300, all such features can be included in an embodiment, and the inclusion of the described features is considered optimum for configuring the plate to the medial surface of the distal humerus and for supporting fractures thereat.

Figure 14:
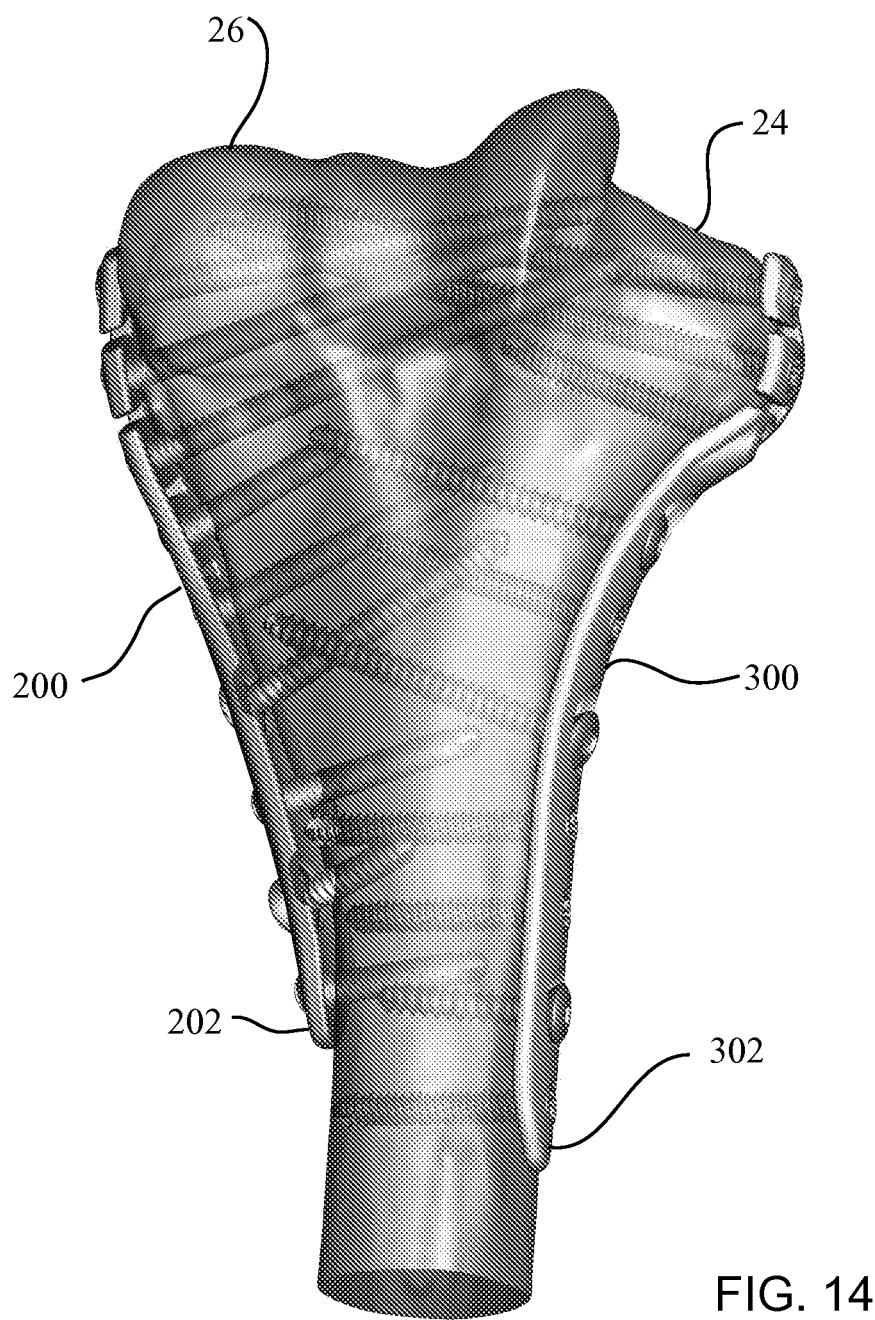
FIG. 14 is an anterior, transparent view of the distal humerus with the lateral and medial plates of FIGS. 11 and 12 attached thereto by a plurality of fasteners.

FIG. 14 is a posterior, transparent view of the distal humerus, showing lateral plate 200 attached near the lateral epicondyle 26 and medial plate 300 attached near the medial epicondyle 24 by a plurality of fasteners. Depending on the type and severity of the fracture, one or both of lateral plate 200 and medial plate 300 may be attached to the distal humeral during the surgical procedure. The lateral and medial plates 200, 300 are located on the humeral bone in a "parallel" configuration, with the plates provided on opposite lateral and medial portions of the bone. The lateral and medial plates 200, 300 are preferably provided in different lengths so that the respective proximal ends 202, 302 of the plates end at different locations on the bone and thereby reduce stress concentrations on the bone. As shown, a combination of cancellous (coarsely threaded) and cortical (finely threaded) fasteners may be used. Lateral plate 200 and medial plate 300 may be provided with fastener holes configured for receiving fixed-angle locking screw 1100, such that the trajectories of the screws are unlikely to intersect. If necessary, however, the surgeon may also attach lateral plate 200 and medial plate 300 to the distal humerus using either of multidirectional locking screw 1000 and multidirectional compression screw 1200. Using conventional, intraoperative fluoroscopic x-ray techniques, the surgeon may insert the fasteners with a desired trajectory to avoid other fasteners and fracture lines and to capture bone fragments.

Bone Plate for the Posterolateral Surface of the Distal Humerus

FIG. 15A is a top perspective view and FIG. 15B is a bottom perspective view of a posterolateral plate 400 for the distal humerus. Posterolateral plate 400 includes a body 406 having a proximal end 402, a distal end 404 and a curvilinear, longitudinal axis 403 extending therebetween. A first arm 410 and a second arm 420 extend from distal end 404 on opposing sides of axis 403, thereby forming a Y-shape. A third arm 430 extends from the body 406 adjacent distal end transversely away from axis 403. Alternatively, third 430 can extend from second arm 420. First arm 410 has a first arm axis 413, second arm 420 has a second arm axis 423 and third arm 430 has a third arm axis 433. Third arm axis 433 is transverse to axis 403, such that third arm 430 may wrap partially around the lateral side of the distal humerus.

Still referring to FIGS. 15A and 15B, first arm 410 includes a first ring element 412 having a hole 414 and is attached to proximal end 404 of body 406 by a first bendable bridge element 416. Second arm 420 includes a second ring element 422 having a hole 424 and attached to distal end 404 by a second bendable bridge element 426. Third arm 430 includes a third ring element 432 having a hole 434 and attached to body 406 by a third bendable bridge element 436. Body 406 includes holes 440, 442, 444, 446 and 448, and an elongated slot 450, each of which may be located along longitudinal axis 403. Each of holes 440, 442, 444, 446, 448, 414, 424 and 434 may be configured with an internal taper thread for receiving any one of multidirectional locking screw 1000, fixed-angle locking screw 1100, or multidirectional compression screw 1200 shown in FIGS. 32, 30 and 35, respectively. Slot 450 may be configured to receive either one of standard compression screw 700 and multidirectional compression screw 1200 shown in FIGS. 27 and 40, respectively. Slot 450 includes cutouts 452 on either side thereof to reduce the stiffness of the body 406 at the slot.

Posterolateral plate 400 also includes two hourglass-shaped openings 454, 456 at the distal side of slot 450. Each opening 454, 456 is substantially similar in design to hourglass shaped slot 238 of lateral plate 200. Such opening 454, 456 reduce the stiffness of the plate between holes to allow the distal end 404 of the body 406 to be reconfigurable using bending tools such as shown in FIG. 5 without a discontinuation of the anterior and posterior edges of the plate as well as retain K-wires for temporary fixation.

FIG. 16 is top perspective view of posterolateral plate 400, shown preassembled with a plurality of first drill guides 1400 (FIG. 41) and second drill guides 1500 (FIG. 43). As described for radial plate 100 in FIG. 5, bending tools 2160, 2180 may be used to reconfigure posterolateral plate 400 while the plate is positioned on the bone surface. In this way, the surgeon may closely match the shape of posterolateral plate 400 to the bone surface and redirect the trajectories of the fasteners to capture bone fragments and avoid fracture lines and other fasteners. Slot 450 is longer than a conventional compression screw slot to reduce the axial torsional stiffness thereat. In this manner, guides in holes 444 and 446 may be used to impart a torque along the axis of the plate to result in an twist to enhance conformation of the plate to the bone, as well as impart a bending force across hourglass-shaped opening 454. Additionally, guides in holes 446 and 448 can be used to impart a bending force across hourglass-shaped opening 456. Third arm 430 is coupled to the body portion 406 near hole 446; thus the plate 400 is highly adjustable in shape on either side of the location at which the third arm 430 is attached. Guides in holes 413, 423, 433, in conjunction with appropriate bending tools, can be used to impart bending forces to reconfigure the orientation of the arms 410, 420, 430 to approximate the ring elements 412, 422, 432 to the bone and redirect the axes through the holes, if necessary. Particularly, arm 430 can be reconfigured to about the humerus to squeeze the lateral condyle 26 and provide lagging.

FIG. 17 is top perspective view of posterolateral plate 400, shown with a plurality of fasteners 441, 443, 445, 447, 449, 415, 425 and 435 fully inserted and locked into holes 440, 442, 444, 446, 448, 414, 424 and 434, respectively. Fastener 451 is fully inserted into slot 450. Each of fasteners 415, 425 and 435, 445 has an axis 419, 429, 439, and 461, respectively, wherein axes 419, 429 and 461 are approximately parallel, and axis 439 extends transverse to axes 419, 429 and 461 and between axes 419, 421 and axis 461.

As shown in FIG. 15B, each of first ring element 410, second ring element 420 and third ring element 430 have a bottom surface 411, 421 and 431, respectively, each of which is configured to conform to the bone surface, but is approximately planar. In order to provide the appropriate fastener trajectory, the thickness of first and second ring elements 412, 422 is greater at a distal region than at a relatively proximal region where the ring elements are coupled to the first and second bridge elements 416, 426. As shown in FIGS. 15B and 17, each of axes 419, 429 and 439 is preferably non-perpendicular to bottom surfaces 411, 421 and 431, respectively, such that the trajectories of fasteners 419, 429 and 439, are optimized for capturing bone fragments and supporting the subchondral surface of the distal humerus. The load from fasteners 415, 425, 435 and 439 is transferred along the plate and to fasteners 441, 443, and 445, where the load is transferred back to the load bearing diaphysis of the humerus.

While it is not necessary to include all of the above described features in the posterolateral plate 400, all such features can be included in an embodiment, and the inclusion of the described features is considered optimum for configuring the plate to the lateral surface of the distal humerus and for supporting fractures thereat.

Figure 18A:
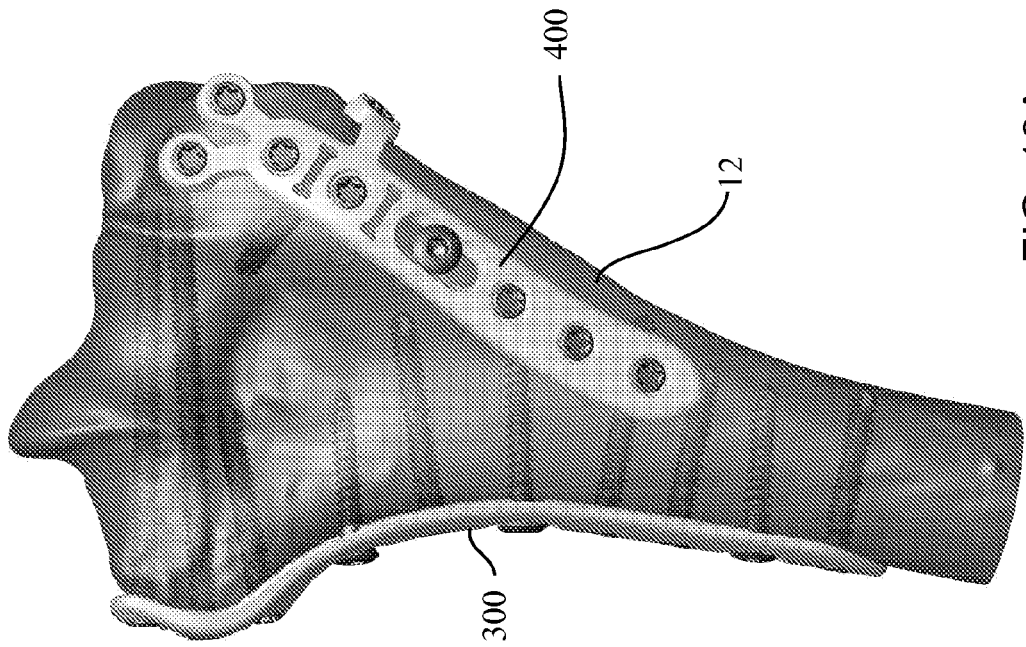
FIG. 18A is posterior, transparent view of the distal humerus with the medial and posterolateral plates of FIGS. 12 and 15A attached thereto by a plurality of fasteners.
Figure 18:
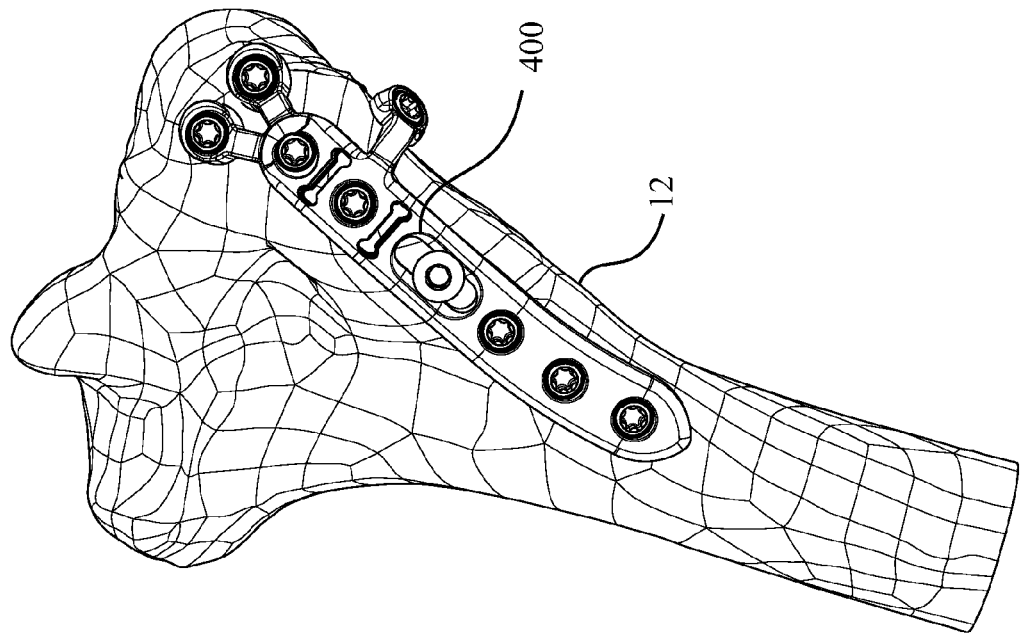
FIG. 18 is a wire frame drawing of the posterolateral plate of FIG. 15A attached to the posterolateral surface of the distal humerus.

FIG. 18 is a wire frame drawing of the posterolateral plate 400 attached to the posterolateral surface of the distal humerus. FIG. 18A is a transparent view showing the medial and posterolateral plates 300, 400 together attached to the distal humerus in a "perpendicular" approach. In this configuration, the medial plate is provided at the medial side of the distal humerus bone while the posterolateral plate is provided at the posterolateral portion of the distal humeral bone. In the perpendicular configuration, loading of the plate is in the direction of the height of the plate. Therefore, the posterolateral plate is substantially thicker than the medial plate. By way of example, the posterolateral plate is preferably approximately 3.5 mm thick; i.e., 1.75 times the thicker than the medial plate). Fracture fixation using the perpendicular approach with the medial and posterior plates provides substantially the same stiffness as the parallel approach with the lateral and medial plates 200, 300.

Bone Plate for the Coronoid of the Proximal Ulna

Figure 19:
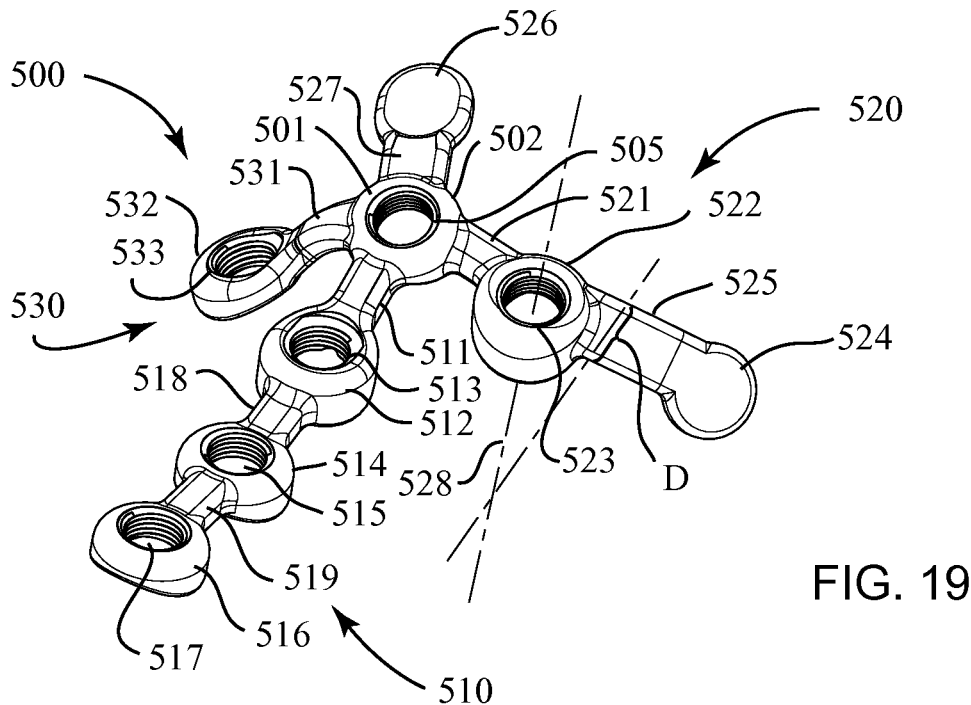
FIG. 19 is a top perspective view of a coronoid plate.
Figure 20:
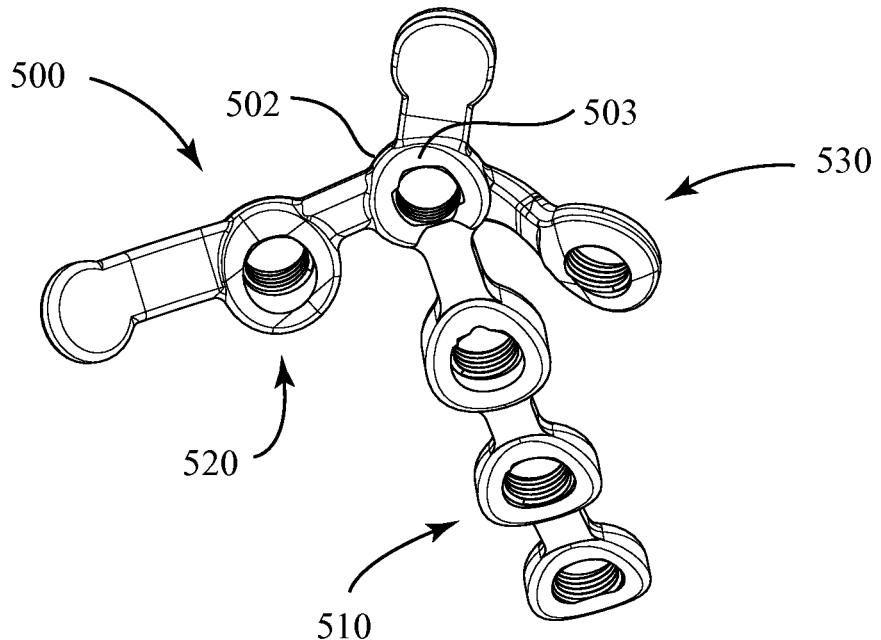
FIG. 20 is a bottom perspective view of the coronoid plate of FIG. 19.
Figure 21:
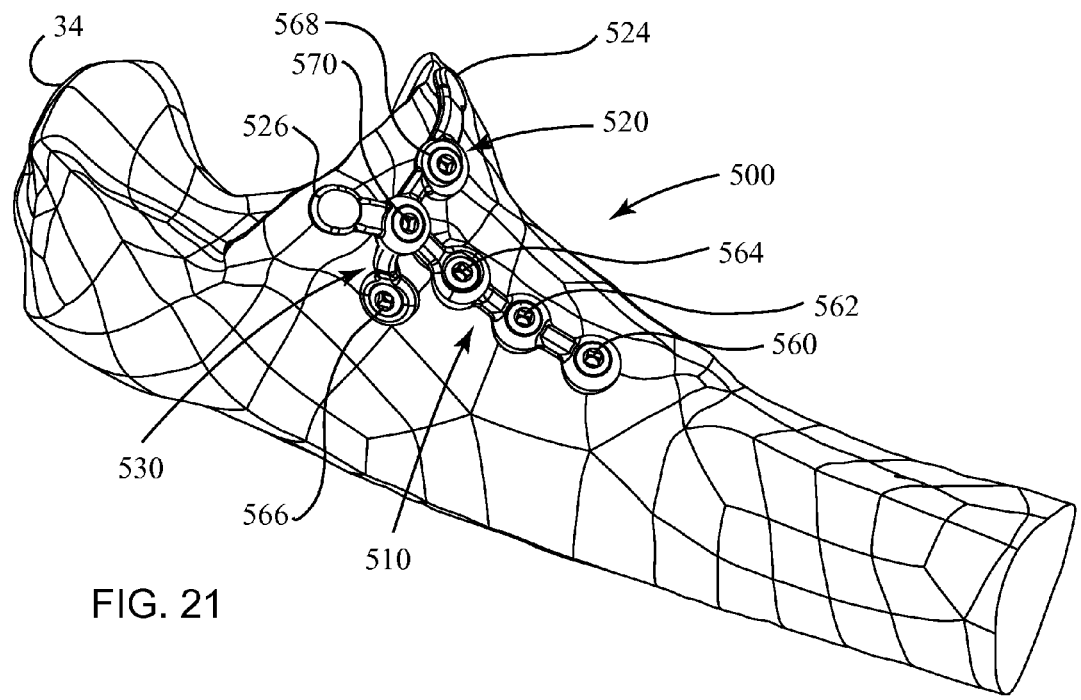
FIG. 21 is wire frame view of the coronoid plate of FIG. 19 attached to coronoid of the proximal ulna.

FIG. 19 is a perspective view of a top surface 501 of a bone plate 500, also called a coronoid plate 500, for the coronoid of the proximal ulna. The coronoid plate 500 is specifically designed to seat on a ridge of the bone. FIG. 20 is a perspective view of a bottom surface 503 of coronoid plate 500. FIG. 21 shows the coronoid plate 500 attached to the proximal ulna. Coronoid plate 500 includes a central ring element 502 containing a hole 505 for receiving a fastener for attachment to the bone. Coronoid plate also includes a first arm 510 extending distally from central ring element 502. In this embodiment, first arm 510 includes a first, a second and a third ring element, 512, 514 and 516, respectively, interconnected in series to central ring element 502 by a first, a second and a third bendable bridge element, 511, 518 and 519, respectively, and having a first, a second and a third hole, 513, 515 and 517, respectively. The lower surface of ring elements 512, 514, 516 is concave in the medial-lateral direction. Referring to FIGS. 1, 2 and 19-22, this forces the plate to align along the coronoid ridge 36 so that fasteners 560, 562, 564 inserted through the holes 513, 515, 517 in first, second and third ring elements 512, 514, 516 will be directed toward surface 38 below the olecranon 34 and lateral to the ridge 40 extending therefrom. This surface 38 has a maximum of soft tissue in the area to cover the ends of any exiting fasteners.

Coronoid plate 500 may also include a second arm 520 extending medially from central ring element 502. Second arm 520 may include a fourth ring element 522 with a fourth hole 523 connected to central ring element 502 by a fourth bendable bridge element 521. Second arm 520 may also include a first buttress element 524 (preferably in the form of a tab or paddle) connected to fourth ring element 522 by a bendable web element 525, thereby extending second arm 520 medially. The upper and lower surfaces of the first buttress element 524 is oriented at an oblique angle (shown by corresponding axis D) relative to the central axis 528 through fourth hole 523 in the fourth ring element 522. First buttress element 524 provides cantilevered support without having to drill a hole, as the surgical approach does not afford suitable access to drill a hole and insert a fastener.

Coronoid plate 500 may also include a third arm 530 extending laterally from central ring element 502. Third arm 530 may include a fifth ring element 532 with a fifth hole 533 connected to central ring element 502 by a fifth bendable bridge element 531.

Coronoid plate 500 may also include a second buttress element 526 connected to central ring element 502 by a second bendable web element 527 and extending proximally. Second buttress element 526 provides support for the sublime tubercle which is too small a fragment for drilling. The relative shapes and sizes of buttress element 526 and web element 527 also permit the structure to be used as an attachment location for suture, which can be wrapped around the web element 527 and sewn into a ligament.

Each of holes 513, 515, 517, 523 and 533 is preferably configured with a tapered thread to receive any one of multi-directional locking screw 1000, fixed-angle locking screw 1100, and multidirectional compression screw 1200. Holes 513, 515, 517, 523 and 533 also may be configured to be preassembled with either one of first drill guide 1400 and second drill guide 1500. As described for radial plate 100 in FIG. 5, bending tools 2160, 2180 may be used to reconfigure coronoid plate 500 while the plate is positioned on the bone surface. In this way, the surgeon may closely match the shape of coronoid plate 500 to the bone surface and also redirect the trajectories of the fasteners to capture bone fragments and to avoid fracture lines and other fasteners.

Bendable web elements 525, 527 may be reconfigured using conventional surgical pliers or the like to position buttress elements 524 and 526 against the bone surface, thereby providing additional support to the healing bone fragments.

Each of bendable web elements 525, 527 and bendable bridge elements 511, 518, 519, 521 and 531 may be easily broken by repeated reverse bending through a significantly large angular range using conventional surgical pliers or the like. The surgeon may easily create the break, such that the broken edge of the implant is directed towards the bone surface in order to prevent injury to surrounding soft tissue. In this way, the surgeon may customize coronoid plate 500 according to the anatomy of the patient.

As shown in FIG. 20, arms 510, 520 and 530, and bottom surface 503 under each of ring elements 512, 514, 516, 522 and 532 may be shaped to closely match the contour of the bone at the coronoid of most patients, although other shapes are possible.

Figure 22:
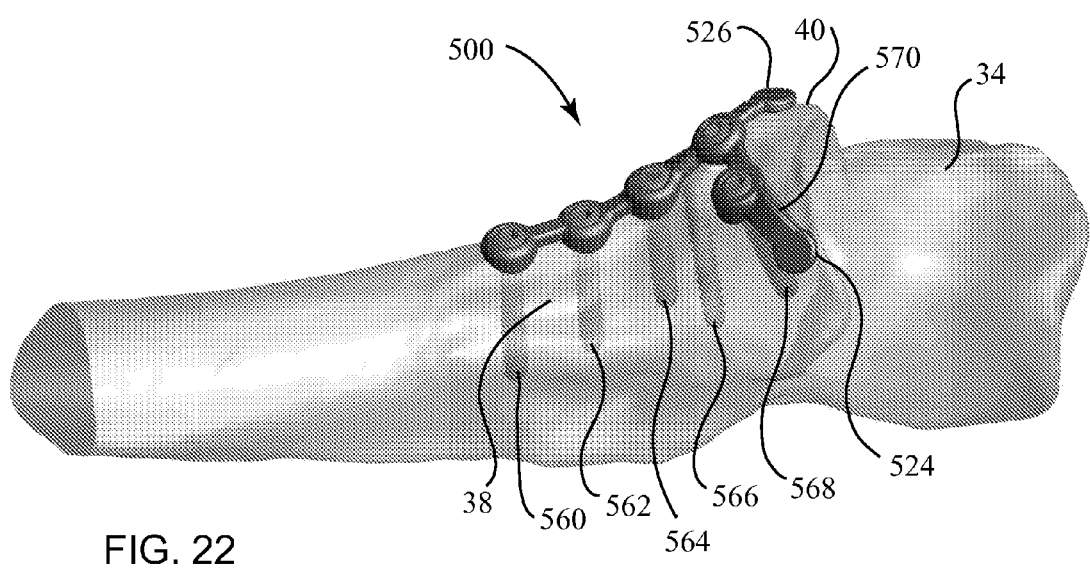
FIG. 22 is a transparent view of the coronoid plate of FIG. 19 attached to the coronoid of the proximal ulna.

FIG. 22 is a perspective, transparent view of coronoid plate 500 attached to coronoid 16 of the proximal ulna. As seen in the figure, four ring elements 502, 512, 514, 516 forming a backbone of the plate sit on a ridge of the bone. This configuration permits relative easy access to plate placement by the surgeon and also allows the plate to be kept away from ligament insertion points and to facilitate. A plurality of bicortical fasteners may be used to create a stable construct for holding bone fragments in healing alignment and sharing the load transferred through the joint. The buttress elements 524, 526 provide the plate 500 with structure that permit fracture support even though there is not commonly ready access to that portion of the bone and where maintaining low profile support is a significant consideration.

The preferred coronoid plate 500 includes a central ring 502 coupled to one arm 532 having a single hole 533, another arm 527 having a single buttress 526 and no hole, another arm having a single hole 523 and a single buttress 524, and another arm having a plurality of holes 513, 515, 517 and no buttress. The coronoid plate 500 functions as a buttress to counteract the tendency of the elbow to subluxate while also holding the small fragments in healing alignment. While the number of arms extending from central ring element 502, the number of ring elements (and holes) interconnected by the bendable bridge elements in each of the arms may vary, and the number of buttresses may vary, the above described configuration of the coronoid plate 500 is preferred as it is considered to be optimum for support of the underlying bone fracture.

Bone Plate for the Olecranon

FIGS. 23A through 25 are views of a bone plate 600 for the olecranon of the proximal ulna. FIG. 23A is a top perspective view and FIG. 23B is a bottom perspective view of the olecranon plate 600, which includes a proximal end 604, a distal end 602 and a longitudinal axis 612 extending therebetween. Olecranon plate 600 includes a body portion 606, a head portion 610 near proximal end 604 and a neck portion 608 connecting body and head portions, 606 and 610. Neck portion 608 is transversely narrower than either of body portion 606 and head portion 610 and increases in thickness toward the head portion. Head portion 608 includes a head axis 614 that is transverse to longitudinal axis 612 of body portion 606. Olecranon plate 600 has a top surface 601, a bottom surface 603, a medial edge 605 and a lateral edge 607.

Body portion 606 may include a plurality of holes 622, 624, 626, 628 for receiving bone fasteners. Body portion 606 may also include at least one slot 634 for receiving a bone fastener and for facilitating the dynamic compression of the fractured bone, as described previously for lateral plate 200 of FIG. 9. Holes 622, 624, 626 and 628 and slot 634 are generally aligned along longitudinal axis 612 and are preferably configured with an internal tapered thread to receive any one of fixed-angle locking screw 1100, multidirectional locking screw 1000 and multidirectional compression screw 1200.

Head portion 610 may include at least two holes 630 and 632 aligned on the transverse axis and offset on opposite sides of longitudinal axis 612. Holes 630, 632 may be configured for receiving any one of multidirectional locking screw 1000, fixed angle locking screw 1100, and multidirectional compression screw 1200 of FIGS. 30, 32 and 35, respectively. The axes of holes 630 and 632 are preferably oriented to direct two fixed angle locking screws in slightly divergent trajectories into the olecranon and also to be provide space for the 'home run screw' 650 discussed below.

Olecranon plate 600 may further include a first arm 616 extending medially from medial edge 605 of neck portion 608. First arm 616 includes a first ring element 636 having a first hole 637 for receiving a bone fastener and is attached to neck portion 608 by a first bendable bridge element 642.

Olecranon plate 600 may further include a second arm 618 extending laterally opposite of first arm 616 from a lateral edge 607 of neck portion 608. Second arm 618 includes a second ring element 638 having a second hole 639 for receiving a bone fastener, and is attached to neck portion 608 by a second bendable bridge element 644.

Olecranon plate 600 may further include a third arm 620 extending proximally from head portion 610 and centered on longitudinal axis 612. Third arm 620 includes a third ring element 640 attached to head portion 610 by a third bendable bridge element 645. The third ring element has a third hole 641 for receiving a bone fastener.

Each of holes 637, 639 and 641 of first, second and third arms, 636, 638 and 640, respectively, may be configured to receive any one of multidirectional locking screw 1000, fixed angle locking screw 1100, and multidirectional compression screw 1200.

Referring to FIG. 23B, olecranon plate 600 may also include at least one alignment foot 656 extending downwardly (towards the bone surface) from edge 607 of body 606. Foot 656 aligns the plate relative to an anatomical ridge on the bone. In fact, the foot 656 permits the plate to be aligned blindly (particularly when the surgical wound cannot be opened to expose the entire bone surface) and to maintain plate alignment relative to anatomical landmarks to ensure proper trajectory of bone screws.

FIG. 23C is a bottom perspective view of olecranon plate 600, shown with a plurality of fasteners fully inserted. Notably, second arm 618 is shown without a fastener inserted. Olecranon plate 600 may be used on either one of the right and left arms of the patient, but it is generally not necessary, for a given fracture, to insert a fastener into each of the first and second arms, 616 and 618, in order to form the needed supporting construct in the bone. Therefore, the surgeon may select one of the first and second arms, 616 and 618, to use with a fastener. Optionally, the surgeon may use bending tools 2160, 2180 (FIG. 5) to break off the unused one of first and second arms 616, 618.

As shown in FIG. 23C, an extra long fastener 650, referred to as a "home run screw", may be inserted into third arm 620 to capture the fractured bone fragments and to provide subchondral support. An axis 651 of fastener 650 is generally directed between a pair of axes, 653 and 655, of fasteners 652 and 654, respectively, and preferably at approximately 20° to 45° relative to the longitudinal axis 612 of the plate.

Figures 24, 26:
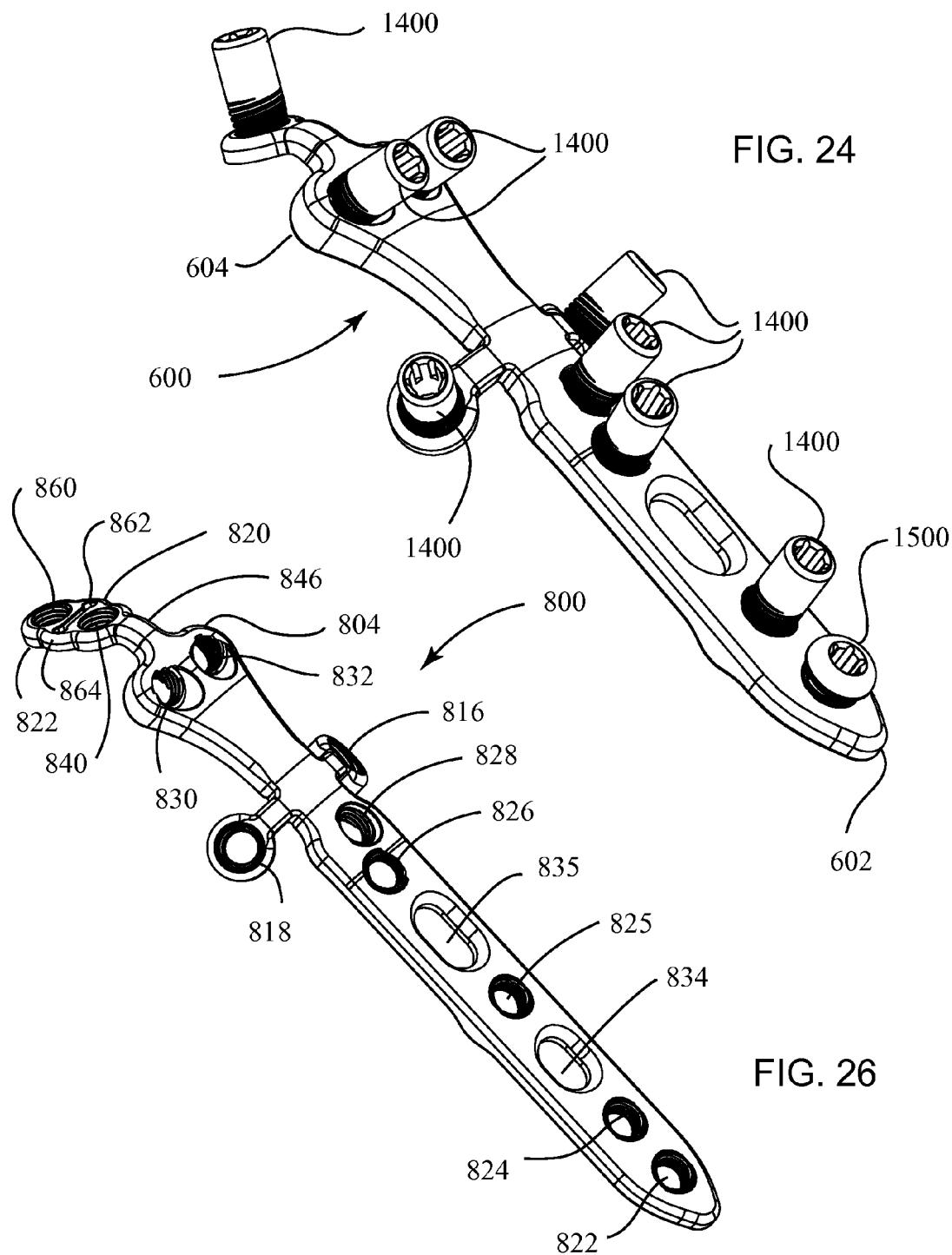
FIG. 24 is top perspective view of the olecranon plate of FIG. 23A preassembled with a plurality of first drill guides of FIG. 41.
FIG. 26 is a top perspective view of another embodiment of an olecranon plate.

As for the other bone plates described herein and shown in FIG. 24, each of the holes in olecranon plate 600 may be preassembled with either of first drill guide 1400 (FIG. 41) and second drill guide 1500 (FIG. 43) to facilitate fastener hole drilling and, if desired, reconfiguration of olecranon plate 600. Referring to FIGS. 23B and 24, third arm 620 is easily reconfigurable in the x-z plane to support the olecranon, such that the trajectory of a fastener inserted into hole 641 passes between the trajectories of fasteners inserted into holes 630 and 632.

Figure 25:
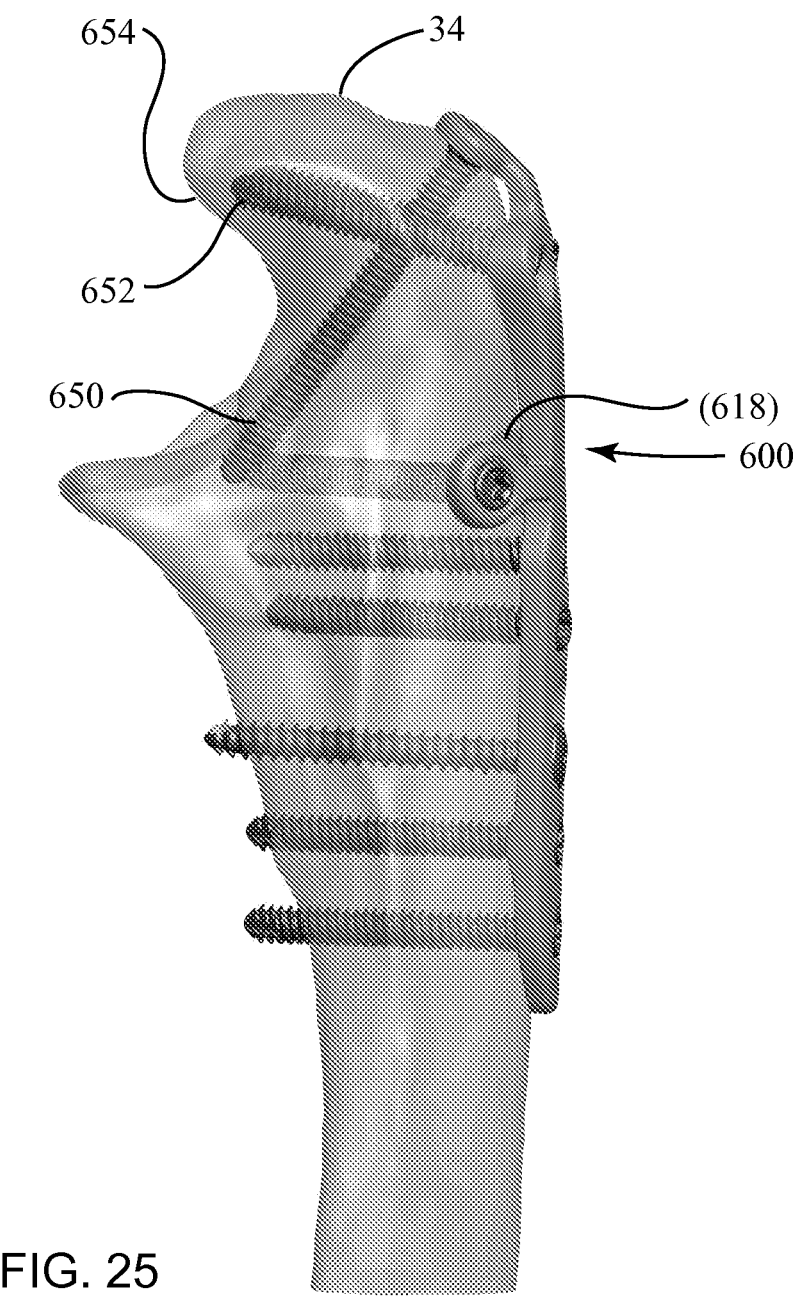
FIG. 25 is a transparent side view of the olecranon plate of FIG. 23A attached to the olecranon of the proximal ulna.

FIG. 25 is a medial side, transparent view of the proximal ulna with olecranon plate 600 attached to olecranon 12. In this example, a fastener is not shown inserted into second arm 618 (hidden), for the reasons already described. Fastener 650 passes between fasteners 652, 654 and through the subchondral bone of the proximal ulna, thereby capturing the fractured bone fragments and allowing olecranon plate 600 to share the forces transmitted through olecranon 12.

FIG. 26 is a top perspective view of a large olecranon plate 800, which is an alternate embodiment of olecranon plate 600. Olecranon plate 800 is configured for larger patients and differs from olecranon plate 600 primarily in overall size and number of holes and slots for receiving fasteners. Olecranon plate 800 has a third arm 820 that includes a double-ring element 822 with rings 840, 860 attached to a proximal end 804 by a third bendable bridge element 846. Each ring of the double-ring element 822 is attached to the other by two curved segments 862, 864 that permit rings 840, 860 to be closely spaced, but provide a relative large length for relative bending. Double-ring element 822 provides for the insertion of two parallel fasteners (not shown) rather than the single fastener 650 shown in FIG. 23C, or two angled fasteners if guides are inserted into the rings 840, 860 and the axes thereof are bent relative to each other. This permits the large olecranon plate 800 to be configured by the surgeon to conform to unpredictable portions of the olecranon. In addition, two slots 834, 835 are provided. Slot 835 is longer than slot 834.

According to one method for implanting plate 800, two fasteners are inserted through the proximal olecranon at holes 830 and 832. Then a fastener is inserted through shorter slot 834 to reduce the fracture via dynamic compression. The third arm is then bent down, as necessary, to conform to the olecranon and the home run screws are inserted through holes 840 and 860. An additional fastener is optionally inserted through slot 835. The first or second arm 816, 818 and other threaded holes 822, 824, 825, 826, 828 are then provided with fasteners to complete the fixation and load transfer back to the diaphysis.

The embodiments of the olecranon plate shown are structured, and the holes thereof oriented, such that fasteners inserted therein and coupled thereto properly transfer the high forces of the triceps muscle to more distal areas of the ulna. While it is not necessary to include all of the above described features in the olecranon plates 600, 800, such features are included in the preferred embodiments, as such are considered optimum for configuring the olecranon plates 600, 800 to the olecranon of the proximal ulna for supporting fractures thereat.

Fasteners

FIGS. 27 through 40 show four embodiments of bone fasteners (also referred to as screws and pegs) that may be used with radial plate 100, lateral plate 200, medial plate 300, posterolateral plate 400, coronoid plate 500 and olecranon plates 600, 800. The fasteners are described generically since the actual dimensions of each fastener may vary depending on the bone plate and the type of fracture. The type of body thread for each screw may be either one of a cortical thread and a cancellous thread and extend along at least a portion of the screw body. For the fastener embodiments shown that include threaded heads for locking into a threaded hole of the bone plate, the fastener body may be either one of a threaded body or a smooth body.

FIG. 28 is a side view and FIG. 27 is a head end view of a standard compression screw 700 having a head 702 and a threaded body 704. Head 702 has a spherically convex bottom portion 708 that is specifically configured to seat into a spherically concave plate hole to compress the bone plate against the bone, although it is possible to use screw 700 with other types of plate holes. As is well known in the art, screw 700 may also be used in an elongated slot having a spherically concave peripheral wall for dynamic compression, in which the screw provides both a vertically directed force and an axially directed force to the bone plate to aid in the fracture reduction. Head 702 includes a hex drive recess 706, although other recess configurations for other types of drivers is possible. Screw 700 may be formed from a titanium alloy or another metal.

FIG. 29 is a head end view, FIG. 30 is a side view, and FIG. 31 is a detailed view of a multidirectional locking screw 1000 fully inserted into a bone plate 1008 having a tapered threaded hole 1009. Screw 1000 includes a threaded body 1004 and a head 1002 having a square drive recess 1006. Screw 1000 may be locked into plate 1008, such that a screw axis 1010 forms an angle 1015 in the range of 0-15 degrees with a hole axis 1011. Screw 1000 may be formed from a cobalt-chrome alloy that is significantly harder than the plate material, which may be a titanium alloy. Such a multidirectional locking screw is described in detail in U.S. Pub. No. 20070088360A1, which is hereby incorporated by reference herein in its entirety.

FIG. 32 is a perspective view, FIG. 33 is a head end view and FIG. 34 is a detailed cross-sectional view of a fixed angle locking screw 1100, which includes a threaded body 1104 and a tapered threaded head 1102 having a hexabular recess 1106. Screw 1100 may be inserted and locked into a tapered, threaded hole of a bone plate at a fixed angle predetermined by the hole thread axis.

Figure 36:
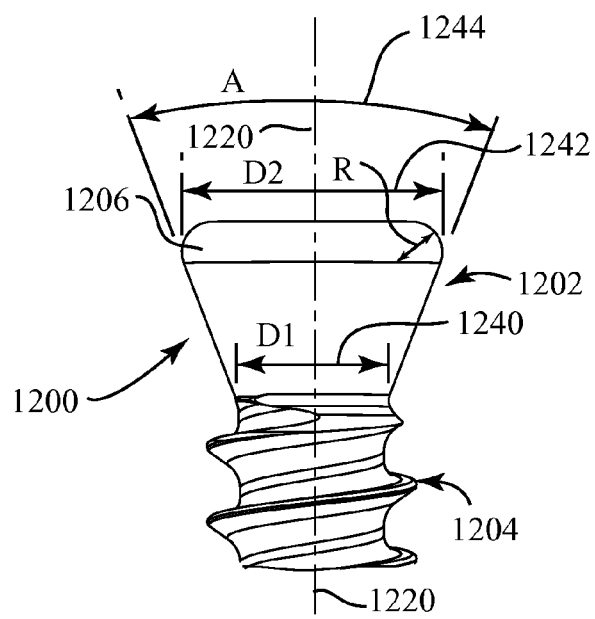
FIG. 36 is a detailed, cross-sectional view of the multidirectional compression screw of FIG. 35.

FIGS. 35 through 38 are views of a multidirectional compression fastener 1200, also called screw 1200. FIG. 35 is a perspective view and FIG. 36 is a detailed view of the proximal portion of screw 1200, which includes a body 1204 having a thread 1206 and a distal tip 1214. Screw 1200 further includes a head 1202 having a proximal face 1208 with a square drive recess 1208, although other drive recess configurations are possible. Head 1202 includes a smooth, frustoconical portion 1212 having a small diameter end 1240 (indicated by D1) attached to body 1204 and a large diameter end 1242 (indicated by D2) forming a peripheral edge 1206 of proximal face 1208. Frustoconical portion 1212 has an included angle 1244 (indicated by A) centered on a screw axis 1220. Peripheral edge 1206 may have an external radius 1242 (indicated by R). Thread 1216 may be one of a cancellous thread and a cortical thread and may be formed into at least a portion of the length of body 1204.

Figure 37:
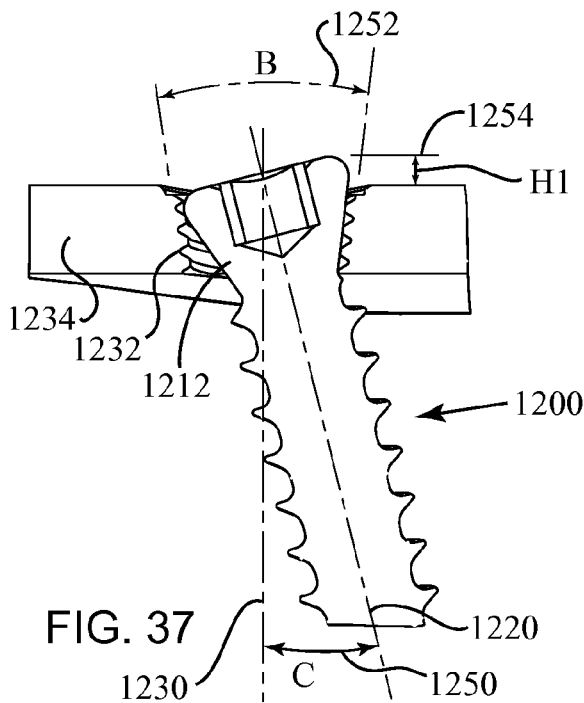
FIG. 37 is a detailed, cross-sectional view of the multidirectional compression screw of FIG. 35 inserted into a bone plate at an insertion angle C.
Figure 38:
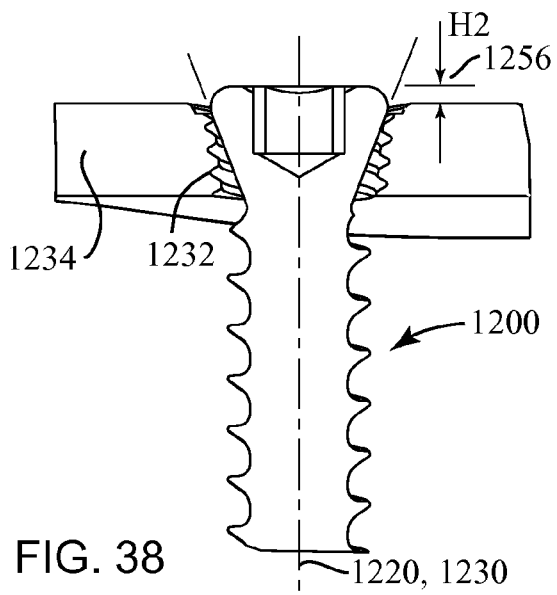
FIG. 38 is a detailed, cross-sectional view of the multidirectional compression screw of FIG. 35 inserted into a bone plate at an insertion angle of zero.

FIGS. 37 and 38 are detailed, cross-sectional views of screw 1200 inserted into a tapered threaded hole 1232 of a bone plate 1234. First referring to FIG. 37, tapered threaded hole 1232 has an included angle 1252 (indicated by B) centered on hole axis 1230. Screw axis 1220 of screw 1200 and hole axis 1230 form an insertion angle 1250 (indicated by C). In this embodiment, insertion angle 1250 may range from 0-15 degrees and is contained by a plane containing hole axis 1230, such that all the possible orientations of screw axis 1220, when fully inserted into hole 1232, define a 30 degree conical volume extending from the bottom of plate 1234. When screw 1200 is fully inserted into hole 1232, frustoconical portion 1212 compresses against hole 1232, but is too large to pass completely through hole 1232. A maximum protrusion height 1254 (indicated by H1) extends above the top surface of plate 1234.

FIG. 38 shows screw axis 120 and hole axis 1230 to be colinear, such that insertion angle is zero. A minimum protrusion height 1256 (indicated by H2) extends above the top surface of plate 1234. In this embodiment, H2 is less than H1, and each of H1 and H2 have an acceptably low profile, such that head 1202 is atraumatic to the surrounding soft tissue.

As will be appreciated by those skilled in the art, the present system described herein provides to a surgeon the advantageous option to use any one of a standard compression screw (screw 700 of FIG. 28), a fixed angle locking screw (screw 1100 of FIG. 33), a multidirectional compression screw (screw 1200 of FIG. 35) and a multidirectional locking screw (screw 1000 of FIG. 30) in the same tapered threaded hole, which is included in each the bone plates described herein. In addition, each of screws 700, 1100, 1200 and 1000 are insertable into the tapered threaded hole, such that the screw head is minimally proud relative to the top surface of the bone plate, thereby minimizing patient discomfort and complications due to soft tissue irritation.

FIG. 39 is a perspective view of a screw head adaptor 1300 provided for use with multidirectional compression screw 1200 of FIG. 35. FIG. 40 shows how adaptor 1300 may be assembled to head 1202 of screw 1200 and then used in a similar manner as standard compression screw 700 of FIG. 27. Adaptor 1300 includes a spherically convex bottom portion 1302 and a rounded upper portion 1304. Bottom portion 1302 and upper portion 1304 form a circular peripheral edge 1312 and together resemble the profile of a standard compression screw head. Adaptor 1300 further includes a bore 1310 having a smooth conical surface 1306 against which head 1202 of screw 1200 is received, such that head 1202 is flush with top portion 1304 of adaptor 1300 when fully inserted.

The screw head adaptor 1300 preferably includes means for engaging the head 1202 of the screw 1200 such that the screw 1200 and adaptor 1300 are assembled to each other to be handled together as a unit during a surgical procedure. According to a preferred embodiment, retaining tabs 1340 are circumferentially displaced about the upper portion of bore 1310. As the screw head 1202 is forced through the adaptor 1300 during assembly, the head 1202 deflects the tabs 1340 radially outward to provide sufficient access for the head 1202 to be received against the conical surface 1306 of the bore 1310, and the tabs 1340 then snap back over the head 1202 to lock the head relative to the adaptor 1300.

Adaptor 1300 and screw 1200 may be used in together as a unit in a plate hole having a spherically concave seating surface to compress the bone plate against the bone. Alternatively, as shown in FIG. 40, adaptor 1300 and screw 1200 may be used in together as a unit, in a compression slot 1235 of a bone plate for dynamically compressing the plate to the bone (in the vertical and axial directions) to assist in fracture reduction. (FIG. 40 may represent both a cross sectional view of a plate hole and a transverse sectional view of a compression slot.) Compression slot 1235 may have a spherically concave, inner cam surface 1233 that engages with bottom surface 1302 of adaptor 1300 to drive bone plate 1232 in a desired direction as screw 1200 is screwed into the bone, such as for further reducing the bone fracture. Screw 1200 may be inserted multidirectionally into the bone at an insertion angle 1308 (indicated by F) defined by screw axis 1220 and slot axis 1330. Insertion angle 1308 may range from about 0 to 15 degrees from slot axis 1330.

Adaptor 1300 may be formed from any one of a number of biocompatible materials, including titanium, a titanium alloy, a stainless steel and a cobalt chrome alloy. Adaptor 1300 may be provide with a smooth, polished finish on all surfaces to facilitate multidirectional insertion of screw 1200 into the bone and dynamic compression of the bone plate against the bone.

Specialized Instrumentation

FIGS. 41 and 42 are perspective views of a first drill guide 1400 having a cylindrical body 1402, a proximal end 1406, a distal end 1404. First drill guide 1400 also has a longitudinal bore 1412 with an axis 1414 and sized for guiding a conventional bone drill. A plurality of internal drive elements 1410 are formed into bore 1412 near proximal end 1406. In this embodiment, the plurality of internal drive elements 1410 include six internal drive elements 1410 for receiving the hexagonally shaped distal tip of a conventional bone screw driver tool, although other configurations and quantities of internal drive elements 1410 are possible. As shown, the internal drive elements 1410 are recessed within the bore 1412 entirely below the proximal end 1406 such that the proximal end of the first drill guide forms a smooth uninterrupted surface surrounding the bore 1412. Furthermore, as shown, each first drill guide 1400 is unitarily formed as a one-piece and as such can be individually handled as a single element.

First drill guide 1400 also has a tapered threaded portion 1408 near distal end 1404 configured for threaded engagement with a tapered threaded hole in a bone plate, such that axis 1414 is colinear with the axis of the tapered threaded hole. The bone plate may be provided to the surgeon with each tapered threaded hole of the bone plate already preassembled with drill guide 1400, so that it is not necessary for the surgeon or an assistant to attach a drill guide to each hole during the procedure as is normally done for conventional bone plating systems. In this way, the surgeon may quickly drill several bone holes, such that the axis of each hole is in perfect alignment with the hole thread axis. The surgeon may then remove the drill guide using the hexagonally tipped driver and insert a locking bone fastener, such that the threaded head of the locking fastener easily engages with the threaded hole. Due to the long, cylindrical shape of body 1402, first drill guide 1400 also may be used with bending tools to reconfigure the bone plate, as was already described for radial plate 100 shown in conjunction with FIGS. 5 and 6, and will also be described for lateral plate 200 in conjunction with FIGS. 50 and 51. The pre-assembly of a first drill guide to a bone plate is described in co-owned U.S. Pub. No. 20060149250A1, and the use of such drill guide for bending a plate is described in co-owned U.S. Pub. No. 20060161158A1, 20070233111A1, and 20070233112A1, all of which are hereby incorporated by reference herein in their entireties.

FIGS. 43 and 44 are perspective views of a second drill guide 1500, which includes a bulbous body 1514, a distal end 1504, a proximal end 1506 and a distal threaded portion 1502. Second drill guide 1500 also includes a cylindrical bore 1512 having a longitudinal axis 1516 and sized for guiding a conventional bone drill. A plurality of internal drive elements 1510 are formed into bore 1512 near proximal end 1506 and may have an identical configuration as internal drive elements 1410 of first drill guide 1400 so that the same hexagonally tipped driver tool may be used, although other configurations and quantities of internal drive elements 1510 are possible. As shown, the internal drive elements 1510 are recessed within the bore 1512 entirely below the proximal end 1506 such that the proximal end of the second drill guide forms a smooth uninterrupted bulbous surface surrounding the bore 1512. Furthermore, as shown, each second drill guide 1500 is unitarily formed as a one-piece and as such can be individually handled as a single element.

Distal threaded portion 1502 is configured for threaded engagement with a tapered threaded hole in a bone plate, such that axis 1516 is colinear with the axis of the tapered threaded hole. As described for first drill guide 1400, a bone plate may be provided to the surgeon with each tapered threaded hole of the bone plate already preassembled with drill guide 1500, so that it is not necessary for the surgeon or an assistant to attach a drill guide to each hole during the procedure as is normally done for conventional bone plating systems. The surgeon may then remove the drill guide using the hexagonally tipped driver and insert a locking bone fastener, such that the threaded head of the locking fastener easily engages with the threaded hole.

Compared to first drill guide 1400, second drill guide 1500 has a low profile once fully inserted into the tapered threaded hole of the bone plate, i.e., second drill guide 1500 is sized for bore 1512 to be sufficiently long to guide the bone drill, yet extend minimally above the top surface of the bone plate so as to facilitate plate insertion with minimal removal of tissue and trauma to tissue. The bulbous or "mushroom" shape of body 1514 facilitates handling and manufacture of second drill guide 1500, and is not intended for removable attachment of the bending tools shown in FIGS. 5, 6, 46, 47 and 48. By way of example, the body of the first drill guide (i.e., that portion which extends above the non-bone contacting surface of plate) has a length of, e.g., approximately 10 to 15 mm, whereas the corresponding body portion of second drill guide has a length of, e.g., approximately 3 to 7 mm. Thus, at at least the smallest and largest respective lengths in the exemplar range, the length of the second drill guide does not exceed one-third to one-half the length of the first drill guide. Also, as clearly shown in FIG. 43, the outer diameter of the second drill guide at the bulbous proximal end of the body substantially exceeds the length of the body of the second drill guide (i.e., again that portion which extends above the distal threaded portion 1502 and thus also above the non-bone contacting surface of plate).

Second drill guide 1500 may be used for portions of the bone plate that are not reconfigurable. As shown in FIG. 45, for example, second drill guide 1500 may be preassembled to lateral plate 200 near proximal end 202, a portion of lateral plate 200 that is not reconfigurable. The low-profile configuration of second drill guide 1500 allows the surgeon to insert proximal end 202 under retracted soft tissue even with second drill guides 1500 attached thereto. This enables the surgeon to make a shorter incision to implant the bone plate than if longer drill guides were used in proximal end 202. In addition, second drill guide 1500 is minimally obstructive to other instruments used in that portion of the wound site during the procedure.

Another type of bending guide may be used which does not include a throughbore. Such guide may have the external (and optionally the proximal internal) characteristics of either the first or second drill guides, but is used only for bending and not for guiding a drill. Such a bending guide may also include an external non-circular cross-section to facilitate instrument force application and/or removal of the bending guide from the plate.

FIG. 46 is a perspective view of the distal portion of a bending tool 1600 that may be used in conjunction with first drill guide 1400 to reconfigure the bone plate. Bending tool 1600 is an alternate embodiment of bending tools 2160 and 2180 shown in FIGS. 5 and 6. The surgeon may use bending tool 1600 for the following: reconfiguring the bone plate to fit the bone more closely; redirecting the trajectory of one or more fasteners; manipulating the bone plate during placement on the bone; and breaking off an unneeded portion of the bone plate. As described earlier for bending tools 2160 and 2180, the surgeon may use a pair of bending tools 1600 to reconfigure the bone plate in situ, i.e., while the plate is positioned on the bone, thereby decreasing the possibility of plate/bone mismatch and reducing the time of the procedure.

Bending tool 1600 includes a handle 1602 having a longitudinal axis 1603 and a distal end effector 1604. Distal end effector 1604 includes a retaining arm 1612 that extends distally and is approximately positioned along the longitudinal axis 1603. Retaining arm 1612 has a retaining bore 1610 with a bore axis 1618 that is transverse relative to longitudinal axis 1603. Bore 1610 is sized to receive body 1402 of first drill guide 1400, such that the surgeon may removably attach end effector 1604 to first drill guide 1400 without applying significant force when bore axis 1618 is colinear with axis 1414 of first drill guide 1400. However, bore 1610 fits slidably over first drill guide 1400, such that applying an appropriately directed force to handle 1602 induces a force couple on first drill guide 1400 in a plane defined by longitudinal axis 1603 and bore axis 1618 (plane x-z as indicated by the coordinate system shown in FIG. 46).

End effector 1604 further includes a first fulcrum 1606 positioned on a first side 1620 of longitudinal axis 1603, and a second fulcrum 1608 positioned on a second side 1622 opposite of first side 1620. Each of first and second fulcrums 1606 and 1608 is proximally offset from bore axis 1618 and contained in the plane defined by the longitudinal and bore axes. First fulcrum 1606 may be further offset than second fulcrum 1608, as indicated by offset 1623 in FIG. 48. This variation in fulcrum offset allows bending tool 1600 to be used on bone plates having varying widths and, in some situations, to have two options for orientation of handle 1402 during use.

FIG. 47 is a perspective view of a pair of bending tools 1600 as they may be used for reconfiguring lateral plate 200 in the x-y plane, as indicated by the coordinate system shown. A first bending tool 1600A is removably attached to a drill guide 1400A preassembled to first segment 212 of lateral plate 200, such that first side 1620A is in the downward direction. A second bending tool 1600B is removably attached to a drill guide 1400B preassembled to distal end 204 of lateral plate 200, such that first side 1620B is in the upward direction. First fulcrum 1606A bears against spine 231 of lateral plate 200. Second fulcrum 1608B bears against medial edge 248 of lateral plate 200. When the surgeon applies equal and same directed forces, indicated by the arrows labeled F1 and F2, in the x-y plane as defined by the coordinate system shown, a leveraging force is applied to spine 231 near first segment 212. In this manner, the surgeon may reconfigure spine 231 near first segment 212. A similar method may be used to reconfigure spine 231 near second segment 214. In order to help hold lateral plate in position on the bone, the surgeon may choose to apply forces F1, F2 after at least one fastener is already inserted in another portion of the plate.

Figure 48:
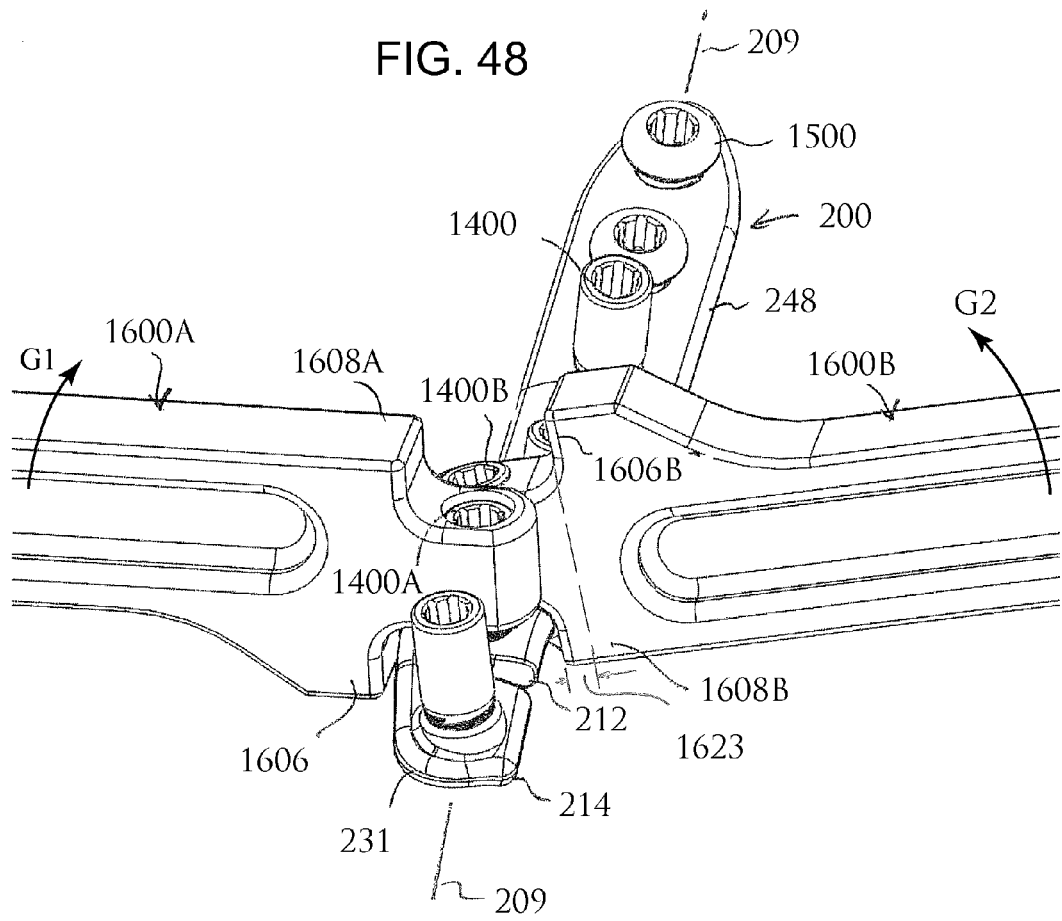
FIG. 48 is a perspective view of the pair of bending tools shown in FIG. 47 as they may be used to reconfigure the bone plate in a y-z plane.

FIG. 48 is a perspective view of a pair of bending tools 1600 as they may be used by a surgeon to reconfigure lateral plate 200 in the y-z plane as indicated by the coordinate system shown. First bending tool 1600A may be removably attached to drill guide 1400A and second bending tool 1600B may be removably attached to drill guide 1400B. For this case, first fulcrum 1606A does not bear against spine 231 and second fulcrum 1608B does not bear against medial edge 248, as in the prior case of FIG. 50. Instead, when the surgeon applies equal and same directed forces G1 and G2 as indicated by the arrows, a force couple is induced in each of drill guides 1400A and 1400B, thereby placing a torque on spline 231 to reconfigure that portion of lateral plate 200.

Figure 49:
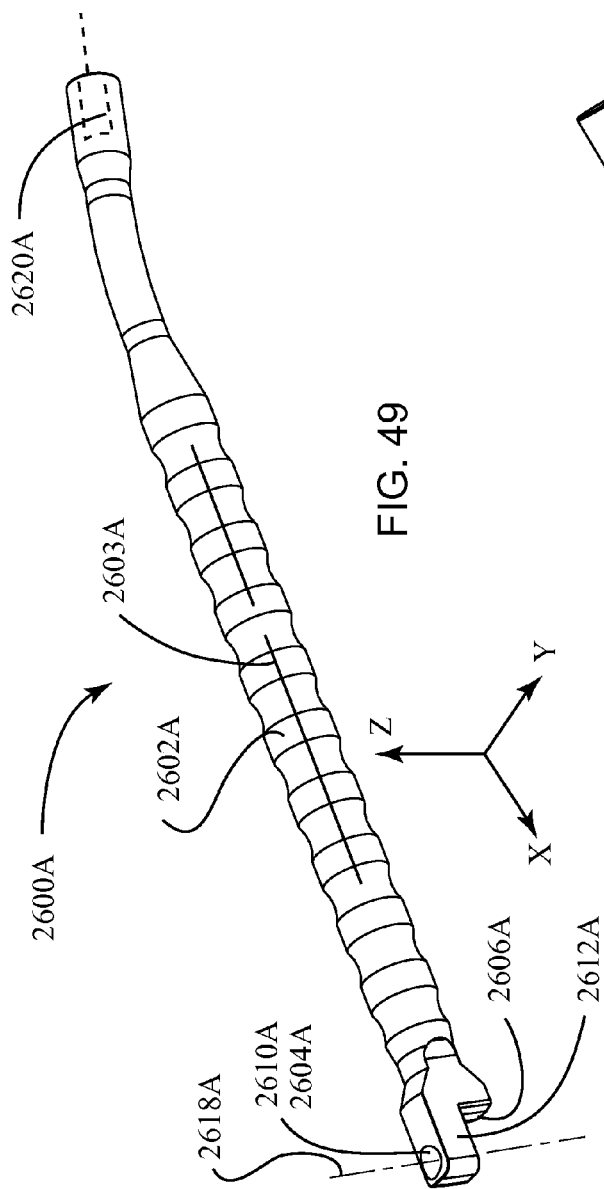
FIG. 49 is a perspective view of a first bending tool of a second embodiment of a pair of bending tools.
Figure 50:
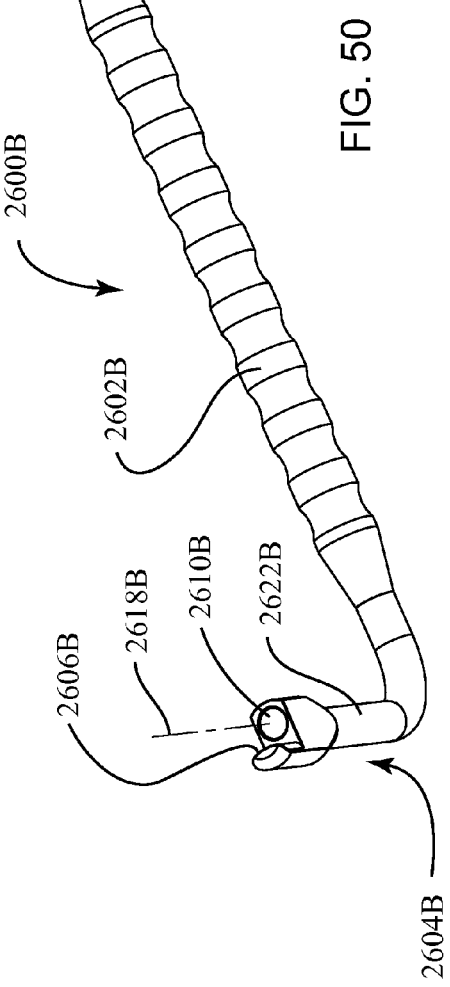
FIG. 50 is a perspective view of a second bending tool of the second embodiment of a pair of bending tools.
Figure 51:
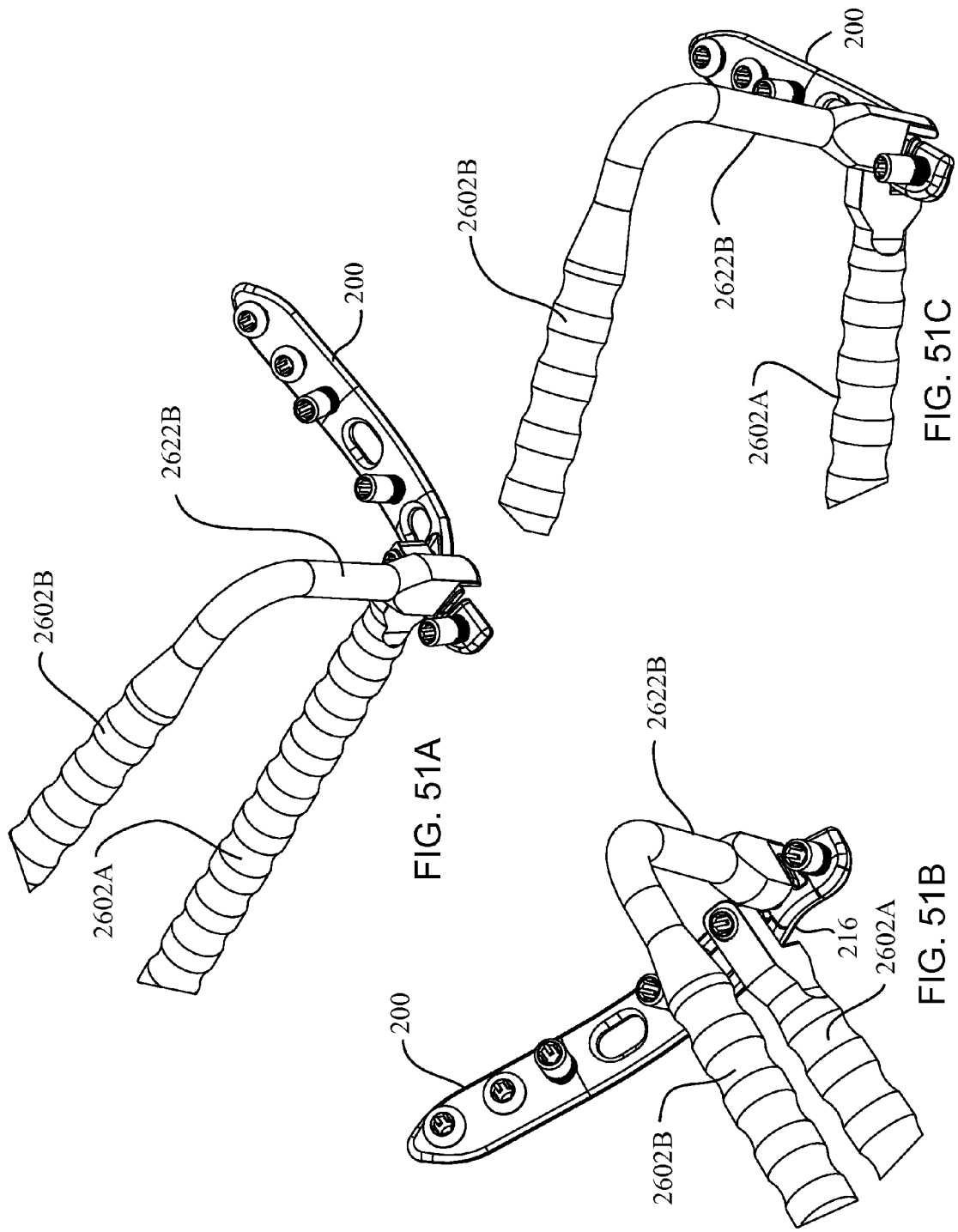
FIGS. 51A-C are perspective views of the pair of bending tools shown in FIGS. 49 and 50 as they may be used to reconfigure the bone plate in a y-z plane.

Turning now to FIGS. 49 and 50, alternate embodiments are shown of bending tools 2600A, 2600B which may be used for the same purpose as bending tools 1600A, 1600B; i.e., in conjunction with first drill guide 1400 and a bone plates to reconfigure the bone plate. As shown in FIG. 49, bending tool 2600A includes a handle 2602A having a longitudinal axis 2603A and a distal end effector 2604A. Distal end effector 2604 includes a retaining arm 2612A that extends distally and is approximately positioned along the longitudinal axis 2603A. Retaining arm 2612A has a retaining bore 2610A with a bore axis 2618A that is transverse relative to longitudinal axis 2603A. Bore 2610A is sized to receive body 1402 of first drill guide 1400, such that the surgeon may removably attach end effector 2604A to first drill guide 1400 without applying significant force when bore axis 2618A is colinear with axis 1414 of first drill guide 1400. However, bore 2610A fits slidably over first drill guide 1400, such that applying an appropriately directed force to handle 2602A induces a force couple on first drill guide 1400 in a plane defined by longitudinal axis 2603A and bore axis 2618A (plane x-z as indicated by the coordinate system shown in FIG. 46). End effector 2604A further includes a convex fulcrum 2606A proximally offset from bore axis 2618A and contained in the plane defined by the longitudinal and bore axes 2603A and 2618A. At the opposite end of the handle 2602A from the end effector 2604A, a bore 2620A is provided coaxial with the longitudinal axis 2603A. The bore 2620A is sized to be slidable received over drill guide 1400.

Referring to FIG. 50, bending tool 2600B is substantially the same as bending tool 2600A with the following distinctions. The end effector 2604B is offset from the handle 2602B by a neck 2622B. The end effector has a bore 2610B with bore axis 2618B parallel to, but not coaxial with, the axis of neck 2622B. The fulcrum 2606B is located at the opposite side of the bore 2610B relative to the handle 2602B and optimally has a smaller offset relative to the bore axis 2618B. Whereas the bending tools 1600A, 1600B are coupled to a plate with the handles 1602A, 1602B extending oppositely from the plate, bending tools 2600A, 2600B are configured such that the handles 2602A, 2602B apply bending force with the tools applied to the same side of the plate. This is useful in certain operating situations, primarily due to space considerations. As shown in FIGS. 51A-51C, this is effected by having the handles 2602A, 2602B of the tools 2600A, 2600B at different heights relative to the plate 200 (by inclusion of the neck 2622B on 2600B only) so as to prevent interference between the handles and of a user's fingers about the handles, and by reversing the location of one of the fulcrums 2606A, 2606B relative to the other. This permits use of the handles to apply force at the fulcrums 2606A, 2606B on opposite sides of bending bridge element 216 to effective reshaping of the plate 200.

Figure 52:
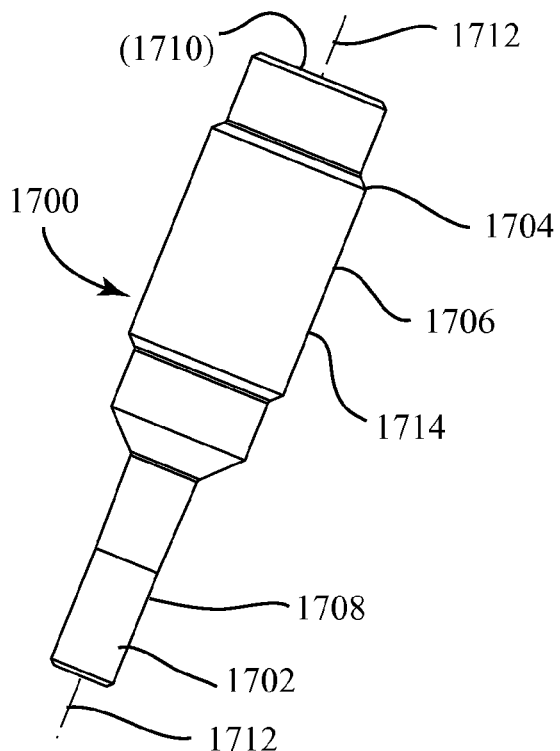
FIG. 52 is a side elevation view of a K-wire insertion tool.
Figure 53:
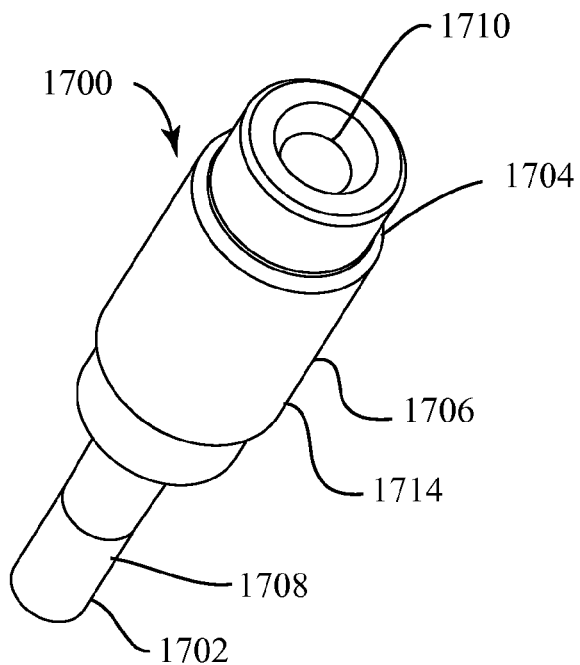
FIG. 53 is a perspective view of the K-wire insertion tool shown in FIG. 52.
Figure 54:
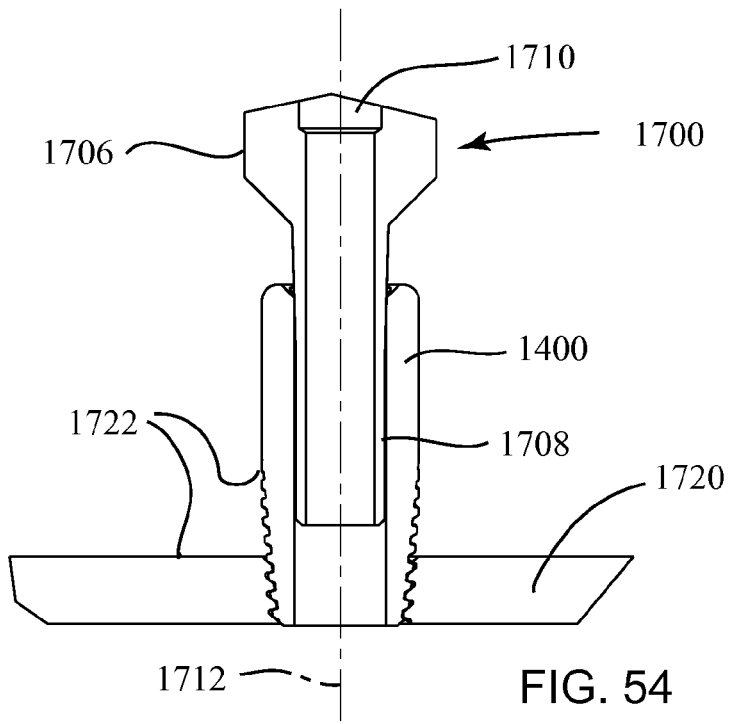
FIG. 54 is a cross-sectional view of the distal portion of the guide wire insertion tool of FIG. 52 removably attached to the first drill guide shown in FIG. 41.

FIGS. 52 and 53 show a K-wire insertion tool 1700. FIG. 54 is a cross-sectional view of the distal portion of tool 1700 removably attached to a preassembly 1722 that includes a bone plate 1720 and drill guide 1400 of FIG. 41. Bone plate 1720 is shown for discussion purposes and may be any one of the other bone plates described herein. The surgeon may use tool 1700 to hold and manipulate preassembly 1722 and also to guide a conventional K-wire along the longitudinal axis of drill guide 1400 and into the bone.

Tool 1700 includes a distal end 1702, a proximal end 1704 and a longitudinal axis 1712 extending therebetween. Tool 1700 further includes a cylindrical body 1714 with a bore 1710 aligned on axis 1712, extending between proximal end 1704 and distal end 1702 and sized to guide a conventional K-wire. Body 1714 includes a proximal gripping portion 1706 and a distal insertion portion 1708.

Gripping portion 1706 may have a cross-sectional diameter, for example, in the range of about 1 to 2 cm and may have a length, for example, about in the range of 3 to 10 cm. Gripping portion 1706 may also be provided with a non-slip gripping surface 1705, which may be a knurled surface or any one of a number of machined surfaces known in the art.

Distal insertion portion 1708 has a cross-sectional diameter that is sized for slidable insertion into and removal from drill guide 1400, yet has sufficient frictional engagement in drill guide 1400 for the surgeon to use tool 1700 to hold and manipulate preassembly 1722. A similar K-wire insertion tool (but which does not extend all the way through the bore of the drill guide) is described in more detail in co-owned U.S. Pub. No. 20080015591A1, which is hereby incorporated by reference herein in its entirety.

While particular embodiments have been described in detail, it is intended that the claimed invention be as broad in scope as the art will allow. Where the terms 'approximate', 'approximately' or 'substantially' are used herein, such terms are to be defined as ±20 percent of a given number, amount, or relative position or location, as determined by context. Those skilled in the art will appreciate that one could make modifications to the devices and methods described herein without deviating from the spirit and scope of the claimed invention.

What is claimed is:

1. A bone plate system for the internal fixation of a fractured long bone, the system comprising:
   a) a metal plate having an upper surface and a bone contacting lower surface, a first end and a second end, said plate defining an arrangement of a plurality of holes at least three of which are threaded holes and one of said threaded holes located adjacent said first end;
   b) a plurality of first-type drill guides, each unitarily formed for handling as a single element, each of said first-type drill guides including:
      i) a tubular body having a proximal end, a distal end, a first length extending between said proximal and distal ends of 10 to 15 mm, and a first outer diameter,
      ii) an axial cylindrical bore extending through said first-type drill guide of a diameter and length for stably guiding a drill,
      iii) an internal non-cylindrical tool engagement feature within said bore at said proximal end of said body for engagement with a tool for applying a rotational force for removal of the drill guide from the threaded hole, and
      iv) a threaded portion extending distally from said distal end of said body to engage said tubular body with said threaded holes such that said proximal end of said body extends above said upper surface of said plate,
      said first-type drill guides being removably preassembled into respective ones of said threaded holes; and
   c) a second-type drill guide of unitarily formed structure that is handled as a single element and consisting essentially of:

i) a body having a rounded, bulbous proximal end, a distal end, a second length extending between said proximal and distal ends of 3 to 7 mm, said body having a second outer diameter larger than said first outer diameter of said of body of said first-type drill guide and larger than said threaded holes of said plate, ii) an axial cylindrical bore extending through said second-type drill guide of a diameter and length for stably guiding a drill, iii) a threaded portion extending distally from said distal end of said body to engage said body with said threaded holes such that said bulbous proximal end of said body extends above said upper surface of said plate, and iv) an internal non-cylindrical tool engagement feature within said bore at said bulbous proximal end of said body adapted for engagement with a tool for applying a rotational force for removal of the drill guide from threaded engagement within the threaded hole, said second-type drill guide being removably preassembled into at least one of said threaded holes including said one of said threaded holes located adjacent said first end of said plate, and wherein both said first-type and second-type of drill guides are preassembled independently and directly to said plate at the same time, and wherein said second-type drill guide has a sufficiently low profile to allow insertion of said first end of said plate under retracted tissue while said second-type drill guide is preassembled within said one of said threaded holes located adjacent said first end of said plate.

2. A system according to claim 1, wherein:
said plate has an end, and said at least three threaded holes includes an end hole adjacent said end, said second type drill guide preassembled into said end hole.

3. A system according to claim 2, wherein:
said plate has a portion of reduced stiffness between said at least two threaded holes in which said first-type drill guides are preassembled.

4. A bone plate according to claim 1, wherein:
said metal plate is machined from a solid bar of fully annealed titanium.

5. A bone plate according to claim 4, wherein:
said metal plate is finished without work hardening.

6. A bone plate system according to claim 1, wherein:
said threaded portions of said plurality of said first-type and second-type of drill guides are tapered.

7. A bone plate system according to claim 1, wherein:
when said second-type of drill guide is preassembled into said respective threaded hole of said plate, said internal tool engagement feature of said second-type of drill guide is located below said internal tool engagement feature of said first-type of drill guide.

8. A bone plate system for the internal fixation of a fractured bone, comprising:

a) a metal plate having an upper surface and a bone contacting lower surface, and defining an arrangement of a plurality of holes at least three of which are holes provided with internal threads defining respective central axes extending through a center of said internal threads;

b) a plurality of first-type drill guides, each of said first-type drill guide including:

i) a cylindrical tubular body defining a proximal end and a distal end, said body having a first length extending between said proximal and distal ends, and said body having a first outer diameter, ii) an axial cylindrical bore extending through said first-type drill guides of a diameter and length for stably guiding a drill, iii) an internal non-cylindrical tool engagement feature within said bore at said proximal end of said body for engagement with a tool for applying a rotational force for removal of the drill guide from the threaded hole, and iv) a threaded portion extending distally from said distal end to engage said tubular body with said threaded holes such that said proximal end of said body extends above said upper surface of said plate, said first-type drill guides being removably preassembled into respective ones of said threaded holes;

c) a second-type drill guide of a unitarily formed structure that is handled as a single element, said guide consisting essentially of:

i) a body having a distal end and a rounded, bulbous proximal end, said body having a second outer diameter larger than said first outer diameter of said body of said first-type drill guide and larger than said threaded holes of said plate, and having a second length extending between said distal and proximal ends, said second length shorter than said first length of said body of said first-type drill guide, ii) an axial cylindrical bore extending through said second-type drill guide of a diameter and length for stably guiding a drill, iii) a threaded portion extending distally from said distal end of said body for engagement with said threaded holes such that said bulbous proximal end of said body extends above said upper surface of said plate, and iv) an internal non-cylindrical tool engagement feature within said bore at said bulbous proximal end of said body adapted for engagement with a tool for applying a rotational force for removal of the drill guide from threaded engagement within the threaded hole, said second-type drill guide being removably preassembled into at least one of said threaded holes; and d) a plate bending tool having a handle extending along an axis at a one end of said tool and an end that attaches to an outer surface of said outside of said cylindrical tubular body of said first-type drill guide and does not attach to an outer surface of bulbous proximal end of said second-type drill guide, said body of said second-type drill guide adapted in size and shape to prevent attachment of the bending tool to the body of said body such that the bending tool is not usable to apply a bending force to the second-type drill guide, and wherein both said first-type and second-type of drill guides are preassembled independently and directly to said plate at the same time.

9. A bone plate according to claim 8, wherein:
said first length is 10 to 15 mm, and said second length is 3 to 7 mm.

10. A bone plate according to claim 8, wherein:
said internal tool engagement feature of said second-type drill guide is recessed entirely within said bore and below said bulbous proximal end of said body so that said proximal end of said second drill guide forms a smooth uninterrupted surface surrounding said axial bore of said second-type drill guide.

11. A bone plate according to claim 8, wherein:
said body of said second-type drill guide has a lengthwise dimension between said upper surface of said plate and said bulbous proximal end, and said second outer diameter exceeds said lengthwise dimension.

12. A bone plate according to claim 8, further comprising:
another second-type drill guide preassembled independently and directly to said plate at the same time as said plurality of first-type drill guide and said other second-type drill guide.

13. A bone plate according to claim 1, wherein:
said body of said second-type drill guide has a lengthwise dimension between said upper surface of said plate and said bulbous proximal end, and said second outer diameter exceeds said lengthwise dimension.

14. A bone plate according to claim 1, further comprising:
another second-type drill guide preassembled independently and directly to said plate at the same time as said plurality of first-type drill guide and said other second-type drill guide.

\* \* \* \* \*

UNITED STATES PATENT AND TRADEMARK OFFICE
CERTIFICATE OF CORRECTION

| | | |
|---|---|---|
| PATENT NO. | : 8,568,462 B2 | Page 1 of 1 |
| APPLICATION NO. | : 12/261392 | |
| DATED | : October 29, 2013 | |
| INVENTOR(S) | : Sixto, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 591 days.

Signed and Sealed this
Seventh Day of April, 2015

Michelle K. Lee
*Director of the United States Patent and Trademark Office*